(12) United States Patent
Jönsson et al.

(10) Patent No.: US 7,074,831 B2
(45) Date of Patent: Jul. 11, 2006

(54) COMPOUNDS, METHODS FOR THEIR PREPARATION AND USE THEREOF

(75) Inventors: Stig Jönsson, Lund (SE); Gunnar Andersson, Röstånga (SE); Ulf Wellmar, Södra Sandby (SE); Ingela Fritzson, Lund (SE)

(73) Assignee: Active Biotech AB, Lund (SE)

( * ) Notice: Subject to any disclaimer, the term of this patent is extended or adjusted under 35 U.S.C. 154(b) by 0 days.

(21) Appl. No.: 11/050,430

(22) Filed: Feb. 4, 2005

(65) Prior Publication Data
US 2005/0187297 A1 Aug. 25, 2005

(30) Foreign Application Priority Data
Feb. 6, 2004 (SE) .................................... 0400234

(51) Int. Cl.
*A61K 31/192* (2006.01)
*C07C 65/105* (2006.01)
(52) U.S. Cl. ...................... 514/563; 548/435
(58) Field of Classification Search ................ 562/435; 514/563
See application file for complete search history.

(56) References Cited

U.S. PATENT DOCUMENTS
4,307,113 A 12/1981 Anderson

FOREIGN PATENT DOCUMENTS
| DE | 2 064 305 | 7/1972 |
| DE | 102 54 872 A1 | 6/2004 |
| EP | 0 034 292 A2 | 8/1981 |
| EP | 0 181 568 A2 | 5/1986 |
| WO | WO 97/28118 A1 | 8/1997 |

OTHER PUBLICATIONS

Sevbo, D.P. et al., 2-Amino-3-phenothiazone deriviatives. III. Methyl 2-amino-3-phenothiazone-1-carboxylate. (1976) Zhurnal Organischeskoi Khimii, vol. 12, No. 8, pp. 1819-15.*
Batt, Douglas G. "Inhibitors of dihydroorotate dehydrogenase" Exp. Opin. Ther. Patents (1999) vol. 9, No. 1, pp.: 41-54.
Breedveld, Ferdinand C. "New Insights in the Pathogenesis of Rheumatoid Arthritis" The Journal of Rheumatology (1998) vol. 25, supplement 53, pp.: 3-7.
Bruneau, Jean-Michel et al "Purification of human dihydroorotate dehydrogenase and its inhibition by A77 1726, the active metabolite of leflunomide" Biochem, J. (1998) 336 pp.: 299-303.
Chan, Dominic M.T. et al "New N- and O-Ariations with Phenylboronic Acids and Cupric Acetate" Tetrahedron Letters 39 (1998) pp.: 2933-2936.
Cherwinski, Holly M. "The Immunosuppressant Leflunomide Inhibits Lymphocyte Proliferation by Inhibiting Pyrimindine Biosynthesis" The Journal of Pharmacology and Experimental Therapeutics, vol. 275, No. 2 (1995) pp.: 1043-1049.
Gennari, Mara et al "Anaerobic Degradation of Acifluorfen by Different Enrichment Cultures" J. Agric. Food Chem, (1994) vol. 42, pp.: 1232-1236.
Hutchinson, John H. et al "Non-Peptide Glycoprotein IIb/IIIa Antagonists. 11. Design and in Vivo Evaluation of 3,4-Dihydro-1(1H)-isoquinolinone-Based Antagonists and Ethyl Ester Prodrugs" J. Med. Chem. (1996) vol. 39 pp.: 4583-4591.
Kubinyl, Hugo "QSAR: Honsch Analysis and Related Approaches" (1993) ISBN 1-56081-768-2 (VCH) "Chapter 3: Parameters" pp.: 21-27.
Mathis, Chester A. "Synthesis and Evaluation of $^{11}$C-Labeled 6-Substituted 2-Arylbenzothiazoles as Amyloid Imaging Agents" J. Med. Chem. (2003) vol. 46, pp.: 2740-2754.
Ohnmacht, Cyrus J. et al "N-Aryl-3,3,3-trifluoro-2-hydroxy-2-methylpropoanamides: KATP Potassium Channel Openers. Modifications on the Western Region" J. Med. Chem., vol. 39 (1996) p. 4592-p. 4601, tables 1-4.
Patil, Sharadbala D et al "Folate Analogues. 32. Synthesis and Biological Evaluation of 2-Desamino-2-methyl-N$^{10}$-propargyl-5,8-dideazafolic Acid and Related Compounds" J. Med. Chem. (1989) vol. 32 pp.: 1284-1289.
Remington's pharmaceutical sciences. Ed. 17, Alfonso R. Gennaro, editor, Easton: Mack Pub. Co., 1985-"Lists of suitable salts are found in . . . ".

(Continued)

Primary Examiner—Kamal A. Saeed
Assistant Examiner—Michael Barker
(74) Attorney, Agent, or Firm—Browdy and Neimark, PLLC

(57) ABSTRACT

Compounds of formula (I)

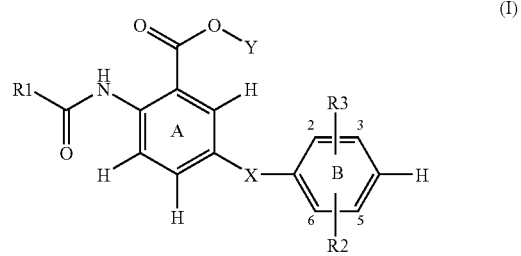

for clinical treatment of autoimmune diseases, inflammatory diseases, organ transplant rejection and malignant neoplasia. A pharmaceutical composition comprising a compound of formula (I) in an amount giving a daily dosage of from 0.005 mg/kg to 10 mg/kg body weight, in particular from 0.025 mg/kg to 2 mg/kg body weight.

17 Claims, No Drawings

OTHER PUBLICATIONS

Research Disclosure Synthetic analogues of the partial structure of the natural product lavendustin A (Author: Novartis Forschungsinstitut GmbH A-I 230 Vienna, Austria) Research Disclosure Database No. 409053. Published in May 1998.

Sevbo, D.P. et al "2-Amino-3-phenothiazone derivatives. III. Methyl 2-amino-3-phenothiazone-1-carboxylate." (1976) Zhurnal Organischeskoi Khimii, vol. 12, No. 8 pp. 1819-1825 ISSN: 0514-7492 *Abstract.

Staiger, Roger P. et al "Isatoic Anhydrde. IV. Reaction with Various Nucleophile" Isatoic Anhydride IV, vol. 24, (Sep. 1959) pp.: 1214-1219.

Vinod Kumar Pandey et al "Synthesis and antiviral activity of quinazolyl thiatriazoles", Acta Pharm. vol. 52, 2002, p. 129-p. 136, compound 1, p. 133.

* cited by examiner

COMPOUNDS, METHODS FOR THEIR PREPARATION AND USE THEREOF

FIELD OF THE INVENTION

The present invention relates to novel anthranilic acid derivatives, which are potent inhibitors of dihydroorotate dehydrogenase (DHODH), to be used for clinical treatment of autoimmune diseases, inflammatory diseases, organ transplant rejection and malignant neoplasia. These compounds and pharmaceutical compositions of this invention are particularly useful for preventing and treating acute and chronic inflammation, rheumatoid arthritis, multiple sclerosis, type-1 diabetes, inflammatory bowel disease, psoriasis, transplant rejection and malignant neoplastic disease. More particularly, the present invention relates to novel derivatives suitable for the treatment of rheumatoid arthritis and transplant rejection.

BACKGROUND OF THE INVENTION

Rheumatoid arthritis (RA) is a chronic inflammatory and destructive joint disease that affects 0.5–1.0% of the population in the industrialised world. RA is a polyarthritis and in the disease virtually all peripheral joints might be affected. Furthermore, extra-articular involvement is another hallmark of RA and this ranges from rheumatoid nodules to life threatening vasculitis. Although the cause of RA remains unknown, autoimmunity plays a pivotal role in its chronicity and progression (Breedveld, 1998). Many pathways involved in the generation of the disease have been recognised and some of these have been unequivocally identified as important by therapeutic proof of principle studies.

Management of RA is a major problem since there is no cure available. Drug therapy for RA rests on two principal approaches: symptomatic treatment with non-steroidal anti-inflammatory drugs (NSAIDs) and disease-modifying anti-rheumatic drugs (DMARDs). NSAIDs only interfere with a small segment of the inflammatory cascade (prostaglandin generation) but do not interfere with the underlying immuno-inflammatory events. By contrast, DMARDs modify the disease process in all these respects. DMARDs can be divided into small molecules and biological agents.

A number of biologicals have recently been approved for clinical treatment of RA. These drugs (proteins, e.g., monoclonal antibodies) prevent in general pro-inflammatory cytokines, in particular TNF-α and IL-1, from interacting with their receptors.

A number of small-molecule DMARDs are used today in RA therapy. In fact methotrexate is still the most commonly used DMARD and sulphasalazine was the second most common DMARD used in Europe during the 1990s. Thus, a number of drugs have been developed and used in RA therapy each targeting a specific pathway of importance to the generation of the disease.

The latest addition to the group of small chemical DMARDs is leflunomide (Merck Index 13$^{th}$ ed No. 5451).

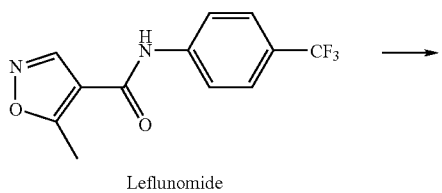

Leflunomide

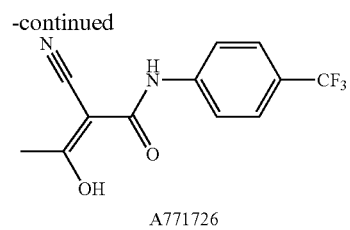

A771726

Leflunomide is in vivo rapidly metabolised to the active metabolite A771726, which inhibits dihydroorotate-dehydrogenase (DHODH), an enzyme that is pivotally involved in de novo pyrimidine synthesis. Inhibition of this enzyme inhibits the growth of (pathologically) fast proliferating cells. The most important cell types for the immune response, the lymphocytes, use exclusively the synthesis of pyrimidines for their growth and react particularly to DHODH inhibition (Batt, 1999; Cherwinski et al., 1995). Substances that inhibit growth of lymphocytes are important medicaments for the treatment of autoimmune diseases including RA. The DHODH inhibiting leflunomide is the first medication of this class of compounds for the treatment of RA. The efficacy of leflunomide in the treatment of RA has been investigated in numerous Phase II and III clinical studies. Leflunomide has provided clinical proof of concept for the mechanism, but due to its side effects, e.g., liver abnormalities and influence on fertility, it is far from optimal for treatment of RA.

EP0497740 discloses benzyloxyphenyl derivatives of general formula (A)

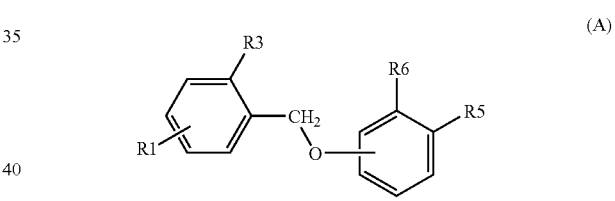

Said patent concerns compounds possessing antihyperproliferative/antiinflammatory and anti-cancer activity. In a preferred group of compounds $R_1$ and $R_3$ are methoxy, and the benzyloxy moiety is in meta-position in respect to $R_6$. $R_6$ is carboxy or an ester group, $R_5$ is hydroxy or acetylamino, especially hydroxy.

EP0815087 discloses trisubstituted phenyl derivatives of general formula (B)

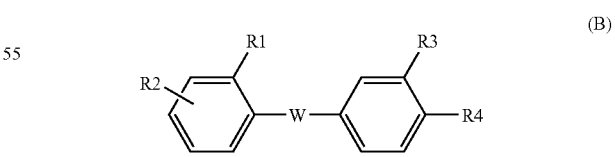

Said patent concerns compounds for the treatment of inflammatory and proliferative skin diseases and cancer. The compounds are to be administered topically or in divided doses up to four times a day. In the most preferred compounds $R_1$ and $R_2$ are methoxy, W is $CH_2CH_2$, and $R_3$ and $R_4$ together with the phenyl ring form a condensed ring system.

Research Disclosure, 1998, 409(May), P561–P562 (No. 40953) discloses synthetic analogues of the natural product Javendustin A, of general formula (C)

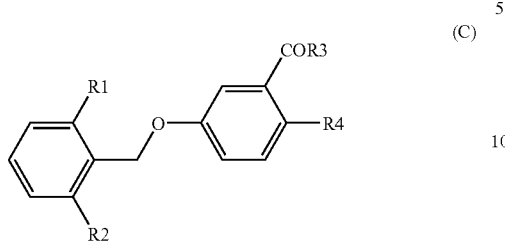

(C)

Compounds are disclosed wherein $R_1$ and $R_2$ are the same or different and represent alkoxy, alkyl or alkenyloxy, $R_3$ is i.a. alkoxy and $R_4$ is i.a. acylamino.

Gennari et al., (1994) reported an anaerobic degradation in soil of 2-nitrophenoxy acids used as herbicides, e.g., acifluorfen, (Merck Index 13$^{th}$ ed. No. 111) that gives compound D.

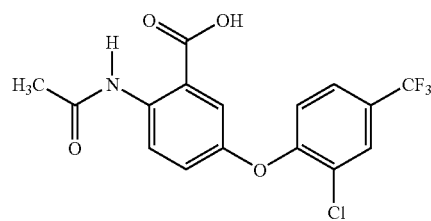

(D)

There is no teaching in the literature disclosing the use of compound D as a pharmaceutical agent.

Symmetrical anthranilic acids of the general formula (E)

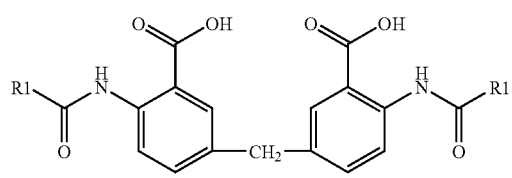

(E)

have been reported in the literature to be used, for example, as high temperature resistant polyheterocycles.

The synthesis of the anthranilic acid of formula (F)

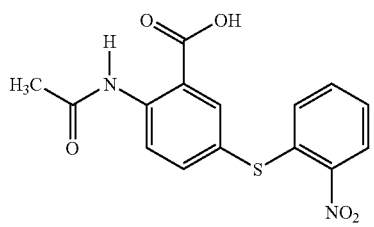

(F)

has been reported by Sevbo et al. (1976). Compound F is used as a synthetic intermediate in the preparation of 2-amino-3-phenothiazone derivatives. There is no teaching in the literature disclosing the use of such intermediate as a pharmaceutical agent.

DESCRIPTION OF THE INVENTION

A primary objective of the present invention is to provide structurally novel anthranilic acid derivatives, which by virtue of their pharmacological profile, with high potency in experimental models and low level of side effects, are considered to be of value in the treatment of auto-immune diseases, inflammatory diseases, organ transplant rejection and malignant neoplasia. In particular, the invention refers to novel compounds, which inhibit DHODH, to a process for their manufacture and pharmaceutical compositions containing them, and to their use for the treatment and prevention of diseases, in particular their use in diseases where there is an advantage in inhibiting DHODH. The compounds may be used for preventing and treating, but not restricted to, acute and chronic inflammation, rheumatoid arthritis, multiple sclerosis, type-1 diabetes, inflammatory bowel disease, psoriasis, transplant rejection and malignant neoplastic disease. More particularly, the present invention relates to novel derivatives suitable for the treatment of rheumatoid arthritis and transplant rejection.

The present invention is directed to compounds of formula (I)

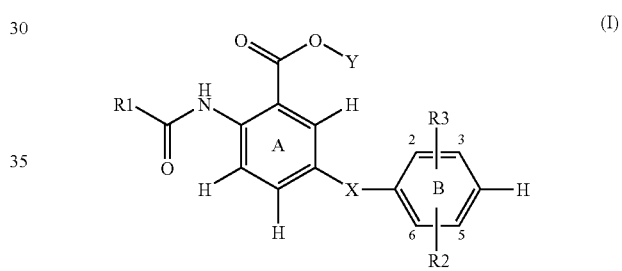

(I)

wherein

X is $CH_2$, NH, O, S, CH=CH, C≡C, $NHCH_2$ or $OCH_2$, wherein the nitrogen or oxygen atom is bound to ring A; $CH_2O$ or $CH_2S$, wherein the oxygen or sulphur atom is bound to ring B;

Y is hydrogen, straight or branched $C_1$–$C_4$ alkyl or a pharmaceutically acceptable inorganic cation;

$R_1$ is ethyl or cyclopropyl;

$R_2$ and $R_3$ are the same or different and represent hydrogen, straight or branched $C_1$–$C_4$ alkylthio, $NHR_4$, $NR_4R_5$, trifluoromethyl, trifluoromethoxy, $NHCOR_6$, phenyl, phenoxy, phenylthio or phenylamino; wherein the phenyl moiety optionally is monosubstituted with fluoro; wherein $R_4$ and $R_5$ independently are hydrogen or straight or branched $C_1$–$C_4$ alkyl; or $R_4$ and $R_5$ together with the nitrogen to which they are bound, form a 5- or 6-membered ring

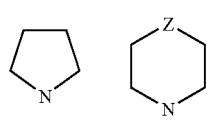

wherein Z is $CH_2$, O, NH or $NCH_3$;

$R_6$ is $C_1$–$C_3$ alkyl, phenylamino, or phenyl optionally monosubstituted with $C_1$–$C_2$ alkoxy or fluoro;

and with the proviso that $R_2$ and $R_3$ are not both hydrogen when X is $OCH_2$;

which are unexpectedly effective as inhibitors of DHODH and lymphocyte cell proliferation.

When Y is a pharmaceutically acceptable cation it may be selected from e.g. $Li^+$, $Na^+$, $K^+$, $Mg^{2+}$, $Ca^{2+}$ and $Zn^{2+}$. In case Y is a divalent cation, it is to be understood that the salt may contain two anthranilic acid derivative moieties for each cation.

In a preferred embodiment of the invention

X is $CH_2$, O, S, CH=CH, $OCH_2$, $CH_2O$ or $CH_2S$;

Y is hydrogen, straight or branched C1–C4 alkyl or a pharmaceutically acceptable inorganic cation;

$R_2$ and $R_3$ are the same or different and represent hydrogen or substituents in the 2-, 3- or 5-positions, selected from $NHR_4$, $NR_4R_5$, trifluoromethyl, trifluoromethoxy, phenyl, phenoxy, phenylthio or phenylamino; wherein the phenyl moiety optionally is monosubstituted with fluoro; and $R_4$ and $R_5$ independently are hydrogen or straight or branched $C_1$–$C_4$ alkyl.

In a more preferred embodiment of the invention

X is O, S, $OCH_2$, $CH_2O$ or $CH_2S$;

Y is hydrogen, or a pharmaceutically acceptable inorganic cation;

$R_2$ is a substituent in the 2- or 3-position and is $NHR_4$, $NR_4R_5$, trifluoromethyl, or trifluoromethoxy;

$R_3$ is hydrogen; and $R_4$ and $R_5$ independently are hydrogen or straight or branched $C_1$–$C_4$ alkyl.

In another more preferred embodiment of the invention

X is O, S, $OCH_2$, $CH_2O$ or $CH_2S$;

Y is hydrogen, or a pharmaceutically acceptable inorganic cation;

$R_2$ is a substituent in the 2-position and is n-propylamino, di-(n-propyl)amino, trifluoromethyl or trifluoromethoxy, and $R_3$ is hydrogen.

In a still more preferred embodiment of the invention

X is $OCH_2$;

Y is hydrogen or a pharmaceutically acceptable inorganic cation;

$R_2$ is a substituent in the 2-position and is trifluoromethyl; and $R_3$ is hydrogen.

In a further preferred embodiment of the invention

X is O;

Y is hydrogen or a pharmaceutically acceptable inorganic cation; and $R_2$ and $R_3$ are substituents in the 3- and 5-positions, and are trifluoromethyl.

Among the most preferred compounds of formula (I) are:

5-benzyl-2-propionylamino-benzoic acid;

2-(cyclopropanecarbonyl-amino)-5-(2-trifluoromethyl-benzyloxy)-benzoic acid;

5-phenylethynyl-2-propionylamino-benzoic acid;

2-propionylamino-5-(2-trifluoromethoxy-phenoxymethyl)-benzoic acid;

2-propionylamino-5-(2-trifluoromethyl-benzyloxy)-benzoic acid;

2-propionylamino-5-(2-trifluoromethyl-phenylsulfanylmethyl)-benzoic acid;

2-propionylamino-5-(2-propylamino-benzyloxy)-benzoic acid;

2-propionylamino-5-(2-propylamino-phenoxy)-benzoic acid;

2-propionylamino-5-(2-propylamino-phenylsulfanyl)-benzoic acid;

2-propionylamino-5-[(E)-2-(2-trifluoromethyl-phenyl-vinyl]-benzoic acid;

5-(2-phenoxy-phenoxy)-2-propionylamino-benzoic acid;

5-(3,5-bis-trifluoromethyl-phenoxy)-2-cyclopropanecarbonylamino-benzoic acid;

5-(3,5-bis-trifluoromethyl-phenoxy)-2-propionylamino-benzoic acid; and 5-(2-dipropylamino-phenoxy)-2-propionylamino-benzoic acid.

The compounds of formula (I) unexpectedly displayed potent inhibition of the enzyme DHODH. The results surprisingly demonstrated an unexpected structure-activity relationship reflecting a specific interaction with the enzyme. Compounds of formula (I) wherein the acylamino group adjacent to the carboxylic acid group was replaced by a hydroxy group demonstrated no DHODH inhibition. Exchanging in a compound wherein the acylamino moiety is acetylamino, the acetylamino moiety for propionylamino or cyclopropylcarbonylamino increased the inhibitory effect up to a 10-fold. Further addition of bulk, however, strongly reduced the DHODH inhibition, reflecting a specific interaction with a size dependent enzyme pocket. Compounds wherein X represents O, S, CH=CH, $OCH_2$, $CH_2O$ or $CH_2S$ demonstrated particularly high potency as inhibitors of DHODH. The type and position of the $R_2/R_3$ substitution was found to be crucial for a strong DHODH inhibition. Compounds wherein $R_2/R_3$ are lipophilic substituents with high π-values in the range 0.5 to 2 (Kubinyi, 1993) displayed maximal inhibition. Moreover, monosubstitution, i.e., $R_3$ is hydrogen, was superior to di-substitution. The position of the monosubstitution was important for the effect, i.e., the ortho-substitution was superior to meta-substitution, and far superior to substitution in the para-position. The type and position of the $R_2/R_3$ substitution did also affect the pharmacokinetic profile.

Synthetic Procedures

The compounds of formula (I) may be prepared by the following methods:

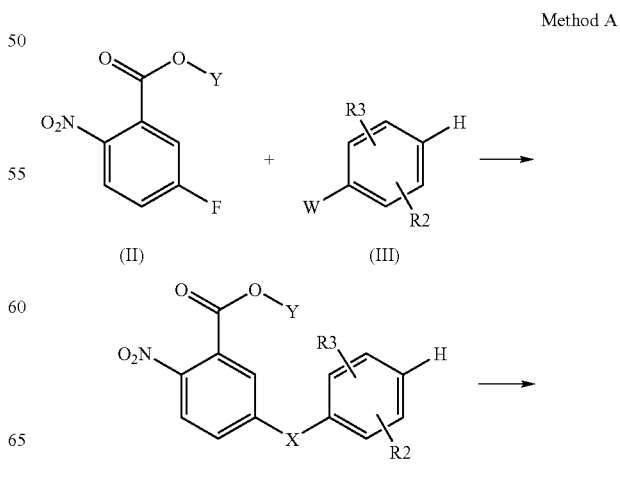

Method A

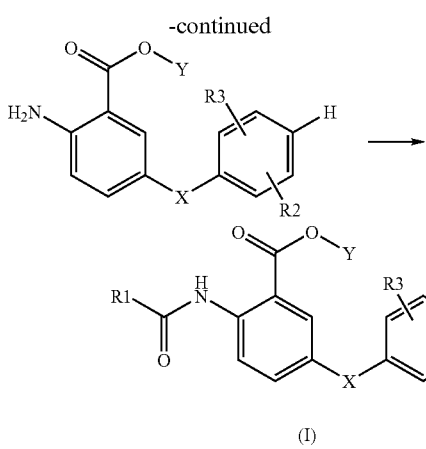

(I)

The compounds of formula (I) may be prepared by known methods, for example, by aromatic nucleophilic substitution of nitro-activated fluoro derivatives (II) in a suitable solvent such as acetonitrile or apolar aprotic solvent, e.g., DMF. Suitable reactants (III) are for example, aryl thiols and phenols (W=OH or SH) in the presence of an alkaline salt such as potassium or cesium carbonate. The reduction of the resultant nitro derivative to corresponding amino derivative may be accomplished by use of anhydrous copper(II)acetate activated sodium borohydride in ethanol at room temperature. This reduction agent is particularly useful for reduction of sulphur containing nitro derivatives as described by Mathis et al. (2003). The resultant amino derivative may be readily transformed to target compound (I) by acylation. Suitable acylating reagents are for example anhydrides and acyl chlorides (Method J). Simple alkaline hydrolysis of the ester functionality provides the acidic function.

Method B

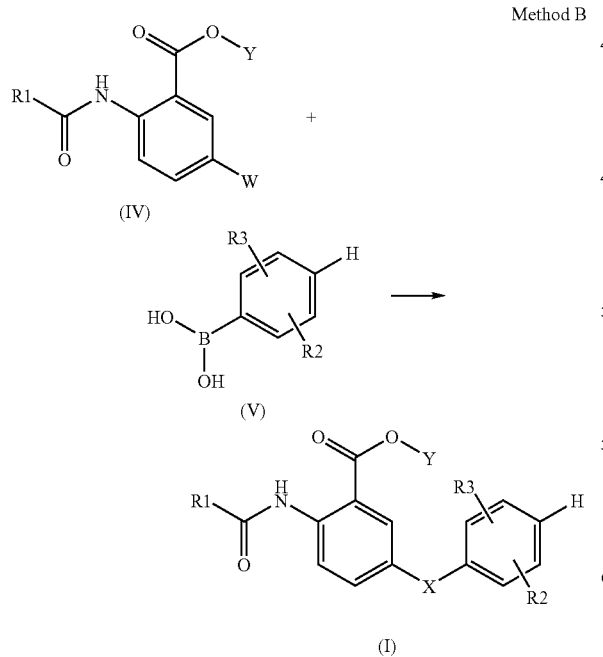

The compounds of formula (I) may also be prepared by N- and O-arylation of substituted anilines or phenols (W=NH₂ or OH) with a phenylboronic acid (V) for example using the procedure described by Chan et al. (1998). The yields are generally in the range of 5–80%, with lower yields for ortho-substituted aryl compounds. Simple alkaline hydrolysis of the ester functionality provides the acidic function.

Method C

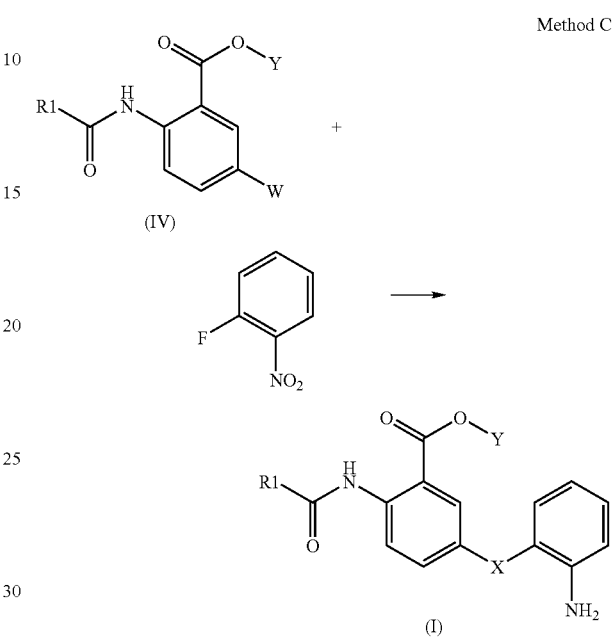

Aromatic nucleophilic substitution may also be applied in the preparation of 2-substituted amino derivatives. The reaction conditions are similar to the conditions in method A, with a good yield of the intermediate nitro derivative. This may then be reduced to the corresponding amino derivative, which may be reacted with phenylboronic acid derivatives as described in Method B, or alkylated via reductive alkylation as described in Method D.

The compound of formula (I) wherein R₂ is NH₂ may be further transformed by acylation thereof. Suitable acylating reagents are for example anhydrides and acyl chlorides (Method J). Simple alkaline hydrolysis of the ester functionality provides the acidic function.

Method D

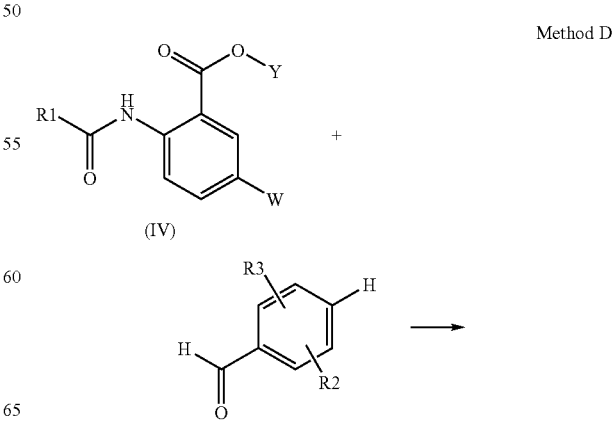

-continued

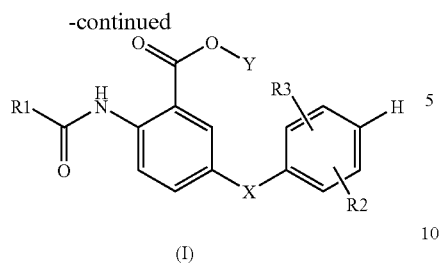

(I)

Compounds with X=NHCH$_2$ may be prepared by reacting a compound of formula (IV) (W=NH$_2$) with an aromatic aldehyde under reductive conditions. Simple alkaline hydrolysis of the ester functionality provides the acidic function.

Method E

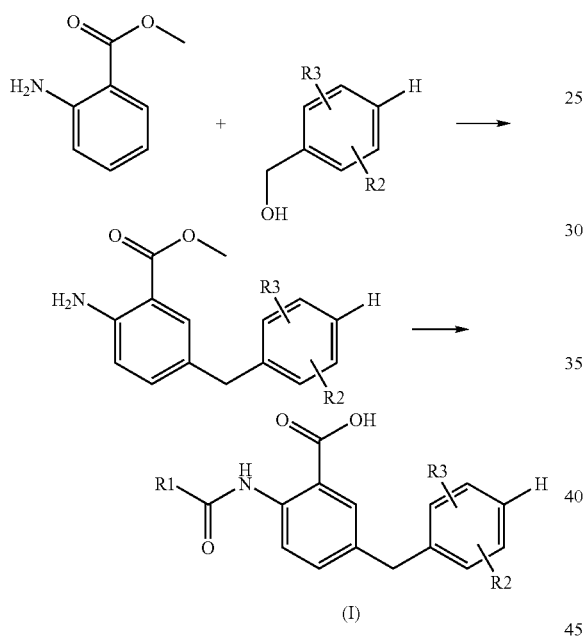

Compounds with X=CH$_2$ (formula (I)) may be prepared according to the method described by Freitag (1970). Thus, methyl anthranilate may be condensed with the appropriate benzyl alcohol under heating. The yields are generally low. The formed 5-substituted anthranilic ester may then be acylated and the ester optionally hydrolysed.

Method F

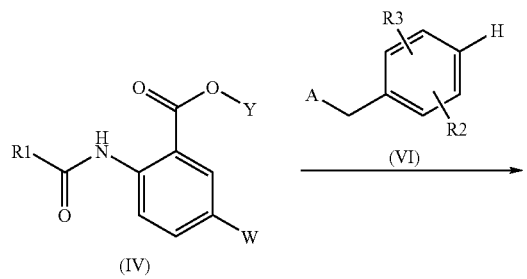

-continued

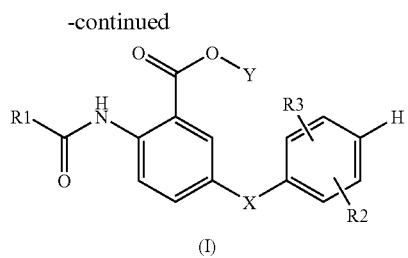

(I)

The compounds of formula (I), may also be prepared by reacting a compound of formula (IV) or corresponding acid, wherein W is a nucleophilic group, with a benzylic reagent wherein A is a leaving group, e.g., bromide, chloride, mesyloxy or tosyloxy. The substitution may be carried out in a suitable solvent such as a polar aprotic solvent, e.g., acetone or DMF, in the presence of an alkali metal carbonate, e.g., potassium carbonate. Simple alkaline hydrolysis of the ester functionality provides the acidic function.

Method G

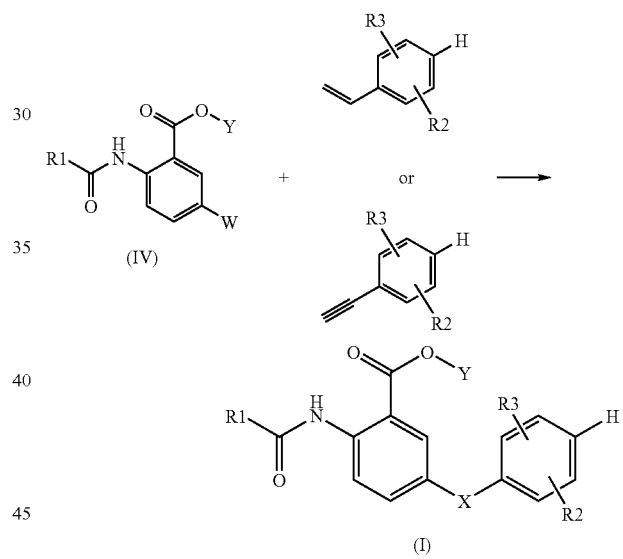

Compounds with X=CH=CH or C≡C may be prepared by reacting a compound of formula (IV) (W=Br) with a styrene (Heck-reaction) or a phenyl acetylene (Steven-Castro-coupling) with palladium catalysis. Simple alkaline hydrolysis of the ester functionality provides the acidic function.

Method H

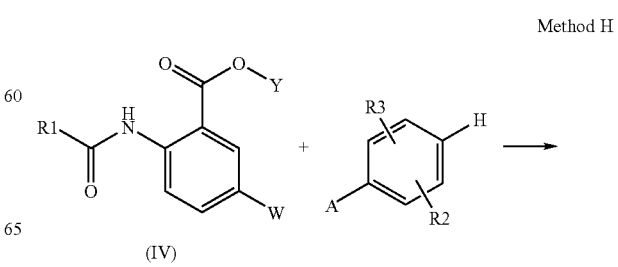

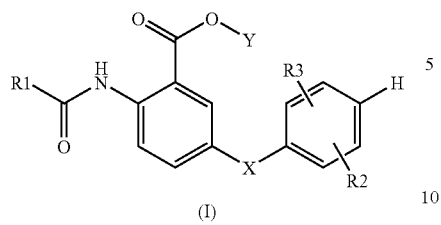

(I)

The compounds of formula (I) may also be prepared by reacting a compound of formula (IV) (W=CH₂Br) with a phenol or thiophenol (A=OH or SH). Simple alkaline hydrolysis of the ester functionality provides the acidic function.

Method I

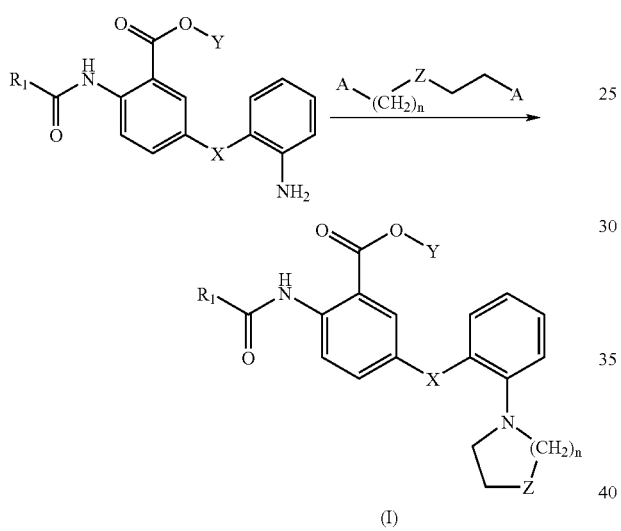

(I)

The compounds of formula (I) may also be prepared by N-alkylation of anilines with an α,ω-difunctionalized alkyl-moiety (Z=CH₂ when n=1, 2; or Z=NH, NCH₃, O when n=2) wherein A is a leaving group, e.g., bromide, chloride, mesyloxy or tosyloxy as described by Hutchinson et al. 1996. Simple alkaline hydrolysis of the ester functionality provides the acidic function.

Method J

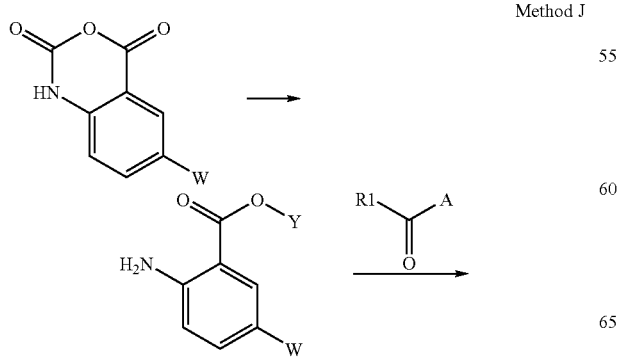

(IV)

The N-acylanthranilic ester (IV) may be prepared from commercially available isatoic anhydrides or by reacting commercially available 5-substituted anthranilic acids with phosgene to provide isatoic anhydrides. The reaction of an isatoic anhydride with anhydrous alcohols, in the presence of small quantities of sodium methoxide provides the corresponding anthranilic ester in a good yield (Staiger and Miller, 1959). Suitable acylating reagents to transform the anthranilic ester to the amide (IV) are for example acid anhydrides and acyl chlorides (A is a leaving group).

Method K

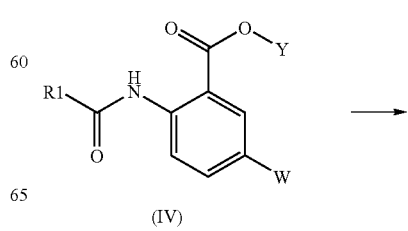

(IV)

Compounds of formula (IV) may also be prepared from commercially available 5-substituted anthranilic acids. Reaction of such an acid with anhydrous alcohols in the presence of thionyl chloride provides the anthranilic ester which then can give amides IV according to method J.

Method L (IV)

-continued

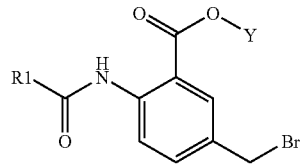

Compounds of formula (IV) (W=CH$_3$) may be transformed to the corresponding 5-benzyl bromide with 1,3-dibromo-5,5-dimethyl hydantoin (Patil et al. 1989).

The following examples illustrate the present invention, but are not to be construed as limiting the scope of the invention.

In the Examples below AutoNom Standard was used to generate the compound names.

In general, nuclear magnetic resonance data were recorded at 400 MHz using a Bruker ARX 400 spectrometer. The spectra were obtained in CDCl$_3$, CD$_3$OD and DMSO-d$_6$ and the shift scale was referenced to TMS, defined as 0.00 ppm. Abbreviations used in the description of NMR spectra were: s=singlet, d=doublet, t=triplet, q=quartet, m=multiplet, b=broad, bs=broad singlet, dd=double doublet and dt=double triplet.

EXAMPLE 1

2-Propionylamino-5-(2-trifluoromethyl-phenylsulfanyl)-benzoic Acid

A mixture of 5-fluoro-2-nitrobenzoic acid (1.9 g, 10 mmol), 2-(trifluoromethyl)thiophenol (2.0, 11 mmol), potassium iodide (0.8 g, 5 mmol) and cesium carbonate (6.5 g, 20 mmol) was heated at reflux in acetonitrile (60 mL) for 10 minutes. The reaction mixture was then cooled and the precipitate collected by filtration. This material was worked up with 1 M HCl (20 mL) and CH$_2$Cl$_2$ (50 mL), the organic layer was washed with brine solution (20 mL), dried over MgSO$_4$ and evaporated to dryness, leaving a yellow solid (3.0 g, 8.7 mmol) of 2-nitro-5-(2-trifluoromethyl)-phenylsulfanyl-benzoic acid. This crude product was dissolved together with anhydrous copper(II)acetate (1.7 g, 8.7 mmol) in ethanol (50 mL). Sodium borohydride (3.4 g, 87 mmol) was then added in portions over 10 min. After 1 h, the solvent was evaporated, the residue was treated with cold 0.5 M HCl and the mixture was extracted with ethyl acetate. The collected black organic phase was dried, filtered through a short column of silica gel and the solvent was evaporated to afford a yellow solid (2.1 g, 6.8 mmol) of 2-amino-5-(2-trifluoromethyl)-phenylsulfanyl-benzoic acid. This was treated with propionic anhydride (20 mL), gently warmed and after 1 h treated with hot water (100 mL) under maintained stirring. Upon chilling, the title compound precipitated as greyish crystals 2.5 g (total yield 67%).

$^1$H NMR (CDCl$_3$) δ 1.30 (t, 3H), 2.53 (q, 2H), 7.13 (d, 1H), 7.29 (t, 1H), 7.36 (t, 1H), 7.64 (d, 1H), 7.70 (d, 1H), 8.27 (s, 1H), 8.80 (d, 1H), 11.9 (bs, 1H).

In essentially the same manner the following compounds were obtained from the corresponding starting materials:

2-Propionylamino-5-(3-trifluoromethyl-phenylsulfanyl)-benzoic Acid $^1$H NMR (CDCl$_3$) δ 1.30 (t, 3H), 2.53 (q, 2H), 7.43 (m, 4H), 7.66 (d, 1H), 8.27 (s, 1H), 8.82 (d, 1H).

2-(Cyclopropanecarbonyl-amino)-5-(3-trifluoromethyl-phenylsulfanyl)-benzoic Acid $^1$H NMR (CD$_3$OD) δ 0.99 (m, 4H), 1.75 (m, 1H), 7.24 (d, 1H), 7.41 (t, 1H), 7.49 (t, 1H), 7.61 (dd, 1H), 7.77 (d, 1H), 8.16 (d, 1H), 8.66 (d, 1H).

5-(2-Isopropyl-phenylsulfanyl)-2-propionylamino-benzoic Acid $^1$H NMR (CDCl$_3$) δ 1.24 (d, 6H), 1.28 (t, 3H), 2.50 (q, 2H), 3.53 (m, 1H), 7.13 ( t, 1H) 7.22 (d, 1H), 7.30 (m, 1H), 7.36 (d, 1H), 7.45 (d, 1H), 8.07 (s, 1H), 8.72 (d, 1H), 10.87 (bs, 1H).

2-(Cyclopropanecarbonyl-amino)-5-(2-isopropyl-phenylsulfanyl)-benzoic Acid $^1$H NMR (CDCl$_3$) δ 0.87 (m, 2H), 1.08 (m, 2H), 1.22 (d, 6H), 1.62 (m, 1H), 3.51 (m, 1H), 7.09 (t, 1H), 7.15 (d, 1H), 7.25 (m, 1H), 7.33 (d, 1H), 7.41 (dd, 1H), 8.06 (d, 1H), 8.64 (d, 1H), 11.42 (bs, 1H).

2-Propionylamino-5-(2-trifluoromethoxy-phenylsulfanyl)-benzoic Acid $^1$H NMR (CDCl$_3$) δ 1.30 (t, 3H), 2.54 (q, 2H), 7.04 (d, 1H), 7.16 (t, 1H), 7.25 (m, 2H), 7.67 (dd, 1H), 8.29 (d, 1H), 8.82 (d, 1H), 11.01 (bs, 1H).

EXAMPLE 2

2-Propionylamino-5-(2-propylamino-phenoxy)-benzoic Acid

A mixture of 5-hydroxy-2-propionylamino-benzoic acid methyl ester (1.0 g, 4.5 mmol) and potassium carbonate (0.62 g, 4.5 mmol) was stirred in DMF (5 mL) for 10 minutes. 2-fluoronitrobenzene (0.63 g, 4.5 mmol) was then added and stirring was continued at room temperature overnight. Water (10 mL) was added and the resulting precipitate was collected by filtration, washed with water and dried under vacuum to give pure 2-propionylamino-5-(2-nitro-phenoxy)-benzoic methyl ester (1.16 g, 3.4 mmol).

$^1$H NMR (CDCl$_3$) δ 1.30 (t, 3H), 2.50 (q, 2H), 3.92 (s, 3H), 6.97 (dd, 1H), 7.22 (dt, 1H), 7.28, (dd, 1H), 7.52 (dt, 1H), 7.75 (d, 1H), 7.97 (dd, 1H), 8.80 (d, 1H), 10.99 (bs, 1H).

This material was dissolved in methanol (50 mL) and 10% Pd/C (116 mg) was added. The flask was then flushed with H$_2$ and stirred at room temperature and at 1 atm. After 5 h of reduction, the catalyst was removed by filtration through Celite. The catalyst was carefully washed and the combined filtrate was evaporated to dryness to give pure 2-propionylamino-5-(2-amino-phenoxy)-benzoic methyl ester compound as a grey solid (0.97 g, 3.1 mmol).

$^1$H NMR (CDCl$_3$) δ 1.29 (t, 3H), 2.48 (q, 2H), 3.89 (s, 3H), 6.72 (dt, 1H), 6.80 (dd, 1H), 6.84 (dd, 1H), 6.99 (dt, 1H), 7.21 (dd, 1H), 7.64 (d, 1H), 8.71 (d, 1H), 10.91 (bs, 1H).

This (200 mg, 0.636 mmol), propionaldehyde (33.3 mg, 0.572 mmol) and acetic acid (1 mL) were stirred together with methanol (20 mL) for 0.5 h. Then, sodium cyanoborohydride (94.3 mg, 0.954 mmol) was added and the mixture was stirred overnight at room temperature. Aqueous saturated sodium bicarbonate (2 mL) was added to the reaction mixture and the methanol was evaporated. The aqueous phase was extracted with ether, and the ether phase was washed with aqueous saturated sodium bicarbonate, dried over sodium sulphate, filtered and evaporated to dryness. Chromatography using silica gel 60 and heptane/ethyl acetate (3:1) as eluent afforded the pure ester product (110 mg). This was hydrolysed in methanol (3 mL) and 1M NaOH (1.5 mL) overnight, acidified with 0.5 M HCl and the product was collected by filtration (90 mg, total yield 54%).

$^1$H NMR (CDCl$_3$) δ 0.98 (t, 3H), 1.28 (t, 3H), 1.66 (m, 2H), 2.48 (q, 2H), 3.14 (t, 2H), 6.67 (t, 1H), 6.79 (m, 2H), 7.07 (t, 1H), 7.26 (m, 1H), 7.67 (d, 1H), 10.78 (bs, 1H).

The following compounds were obtained by reacting the intermediate 2-propionylamino-5-(2-amino-phenoxy)-benzoic methyl ester or 5-(2-amino-phenylsulfanyl)-2-propionylamino-benzoic acid methyl ester (EXAMPLE 17) with boronic acids according to EXAMPLE 6 or with aldehydes as described above.

5-(2-Phenylamino-phenoxy)-2-propionylamino-benzoic Acid $^1$H NMR (CDCl$_3$) δ 1.28 (t, 3H), 2.49 (q, 2H), 6.8–6.9 (m, 2H), 6,99 (t, 1H), 7.06 (m, 1H), 7.16 (m, 2H), 7.26–7.33 (m, 3H), 7.40 (dd, 1H), 7.75 (d, 1H), 8.75 (d, 1H), 10.77 (bs, 1H).

5-[2-(4-Fluoro-phenylamino)-phenoxy]-2-propionylamino-benzoic Acid $^1$H NMR (CD$_3$OD) δ 1.24 (t, 3H), 2.45 (q, 2H), 6.87 (m, 1H), 6.92–6.99 (m, 3H), 7.02–7.09 (m, 3H), 7.14 (dd, 1H), 7.22 (dd, 1H), 7.60 (d, 1H), 8.48 (d, 1H).

5-(2-Ethylamino-phenoxy)-2-propionylamino-benzoic Acid $^1$H NMR (CD$_3$OD) δ 1.23 (m, 6H), 2.43 (q, 2H), 3.19 (q, 2H), 6.61 (dt, 1H), 6.78 (m, 2H), 7.02 (m, 2H), 7.65 (d, 1H), 8.47 (d, 1H).

5-(2-Dipropylamino-phenoxy)-2-propionylamino-benzoic Acid $^1$H NMR (CDCl$_3$) δ 0.81 (t, 6H), 1.27 (t, 3H), 1.46 (q, 4H), 2.48 (q, 2H), 3.18 (t, 4H), 6.91 (d, 1H), 7.03 (t, 1H), 7.11 (m, 2H), 7.18 (d, 1H), 7.80 (d, 1H), 8.68 (d, 1H), 11.29 (bs, 1H).

2-Propionylamino-5-(2-propylamino-phenylsulfanyl)-benzoic Acid $^1$H NMR (DMSO-d$_6$) δ 0.78 (t, 3H), 1.10 (t, 3H), 1.46 (m, 2H), 2.36 (q, 2H), 3.06 (bt, 2H), 5.33 (bs, 1H), 6.62 (t, 1H), 7.71 (d, 1H), 7.29 (dt, 1H), 7.35 (dd, 1H), 7.40 (dd, 1H), 7.65 (d, 1H), 8.38 (d, 1H), 11.01 (bs, 1H).

EXAMPLE 3

5-(2-Butyrylamino-phenoxy)-2-(cyclopropanecarbonyl-amino)-benzoic Acid

A mixture of 5-(2-amino-phenoxy)-2-(cyclopropanecarbonyl-amino)-benzoic acid methyl ester (50.0 mg, 0.153 mmol, prepared according to EXAMPLE 2) and butyryl chloride (23.3 mg, 0.184 mmol) in CH$_2$Cl$_2$ (1.5 mL) was heated in a microwave oven at 110° C. for 10 minutes. The reaction mixture was allowed to reach room temperature and the solvent was removed by evaporation. The crude ester product was hydrolysed in methanol (2 mL) and 1M NaOH (1 mL) over night, acidified with 1M HCl and the product was isolated by filtration (18 mg, total yield: 31%).

$^1$H NMR (CDCl$_3$) δ 0.91 (m, 2H), 0.99 (t, 3H), 1.12 (m, 2H), 1.64 (m, 1H), 1.75 (m, 2H,) 2.38 (t, 2H), 6.79 (d, 1H), 7.01 (t, 1H), 7.13 (t, 1H), 7.29 (dd, 1H), 7.70 (d, 1H), 7.73 (bs, 1H), 8.42 (d, 1H), 8.76 (d, 1H), 11.09 (bs, 1H).

In essentially the same manner the following compounds were obtained from the corresponding starting materials:

2-Propionylamino-5-(2-propionylamino-phenoxy)-benzoic Acid $^1$H NMR (CDCl$_3$) δ 1.26 (m, 6H), 2.47 (m, 4H), 6.79 (d, 1H), 7.02 (t, 1H), 7.14 (t, 1H), 7.31 (dd, 1H), 7.33 (m, 2H), 8.45 (d, 1H), 8.80 (d, 1H), 10.86 (bs, 1H).

5-(2-Benzoylamino-phenoxy)-2-propionylamino-benzoic Acid $^1$H NMR (CDCl$_3$) δ 1.28 (t, 3H), 2.50 (q, 2H), 6.84 (d, 1H), 7.07 (t, 1H), 7.20 (t, 1H), 7.37 (dd, 1H), 7.49 (t, 2H), 7.56 (t, 1H), 7.77 (d, 1H), 7.86 (d, 1H), 8.51 (bs, 1H), 8.62 (d, 1H), 8.82 (d, 1H), 10.84 (bs, 1H).

2-(Cyclopropanecarbonyl-amino)-5-[2-(4-methoxy-benzoylamino)-phenoxy]-benzoic Acid $^1$H NMR (CDCl$_3$) δ 0.86 (m, 2H), 1.05 (m, 2H), 1.60 (m, 1H), 3.79 (s, 3H), 6.85 (dd, 1H), 6.98 (dd, 1H), 7.01 (dt, 1H), 7.11 (dt, 1H), 7.15 (dt, 1H), 7.27 (dd, 1H), 7.46 (dt, 1H), 7.71 (d, 1H), 8.24 (dd, 1H), 8.66 (dd, 1H), 8.68 (d, 1H), 10.70 (bs, 1H), 11.43 (bs, 1H).

2-(Cyclopopanecarbonyl-amino)-5-[2-(3-methoxy-benzoylamino)-phenoxy]-benzoic Acid $^1$H NMR (CDCl$_3$) δ 0.91 (m, 2H), 1.12 (m, 2H), 1.63 (m, 1H), 3.86 (s, 3H), 6.84 (dd, 1H), 7.07 (m, 2H), 7.19 (dt, 1H), 7.38 (m, 3H), 7.44 (bs, 1H), 7.76 (d, 1H), 8.49 (bs, 1H), 8.59 (dd, 1H), 8.78 (d, 1H), 11.05 (bs, 1H).

2-(Cyclopropanecarbonyl-amino)-5-(2-phenylacetylamino-phenoxy)-benzoic Acid $^1$H NMR (CDCl$_3$) δ 0.87 (m, 2H), 1.11 (m, 2H), 1.62 (m, 1H), 3.70 (s, 2H), 6.84 (d, 1H), 7.02 (m, 2H), 7.12 (t, 1H), 7.17 (m, 2H), 7.25 (m, 3H), 7.40 (d, 1H), 7.66 (bs, 1H), 8.27 (d, 1H), 8.67 (d, 1H), 11.33 (bs, 1H).

EXAMPLE 4

5-[2-(3-Phenyl-ureido)-phenoxy]-2-propionylamino-benzoic Acid

A mixture of 2-propionylamino-5-(2-amino-phenoxy)-benzoic acid methyl ester (50.0 mg, 0.153 mmol, prepared as described in EXAMPLE 2) and phenyl isocyanate (21.0 mg, 0.175 mmol) in CH$_2$Cl$_2$ (10 mL) was stirred at room temperature for 2 hours. The solvent was removed by evaporation and the crude ester product was hydrolysed in methanol (1 mL) and 1M NaOH (1 mL) over night. The reaction mixture was acidified with 1M HCl and the product was collected by filtration (54 mg, total yield 80%).

¹H NMR (CDCl₃) δ 1.40 (t, 3H), 2.66 (q, 2H), 6.67 (d, 1H), 6.94 (m, 2H), 7.05 (t, 1H), 7.17 (t, 1H), 7.29 (t, 2H), 7.43 (d, 2H), 7.68 (bs, 1H), 7.95 (bs, 1H), 8.42 (bd, 1H), 8.52 (d, 1H), 10.94 (bs, 1H).

EXAMPLE 5

5-(2-Piperidin-1-yl-phenoxy)-2-propionylamino-benzoic Acid

This compound was prepared essentially as described by Hutchinson et al. 1996. A mixture of 5-(2-amino-phenoxy)-2-propionylamino-benzoic acid methyl ester (1.26 g, 5.00 mmol), 1,5-dibromo-pentane (1.38 g, 6.00 mmol) and ethyl-diisopropyl-amine (2.60 mL, 6.00 mmol) in DMF (30 mL) was stirred at 100° C. for 16 hours. The reaction mixture was allowed to reach room temperature and ethyl acetate (100 mL) was added. The organic layer was washed with aqueous saturated NaHCO₃ and brine and was then dried over MgSO₄, filtered and evaporated to dryness. Chromatography using silica gel 60 and heptane/ethyl acetate (4:1 ->1:1) as eluent afforded a crude product that was again subjected to chromatography using heptane/ethyl acetate (19:1 ->4:1) as eluent, yielding the pure ester product (304 mg). This was hydrolysed in ethanol (2 mL) and 1M NaOH (2 mL) over night, acidified with 1M HCl and the product was isolated by filtration (132 mg, total yield: 7%).

¹H NMR (CDCl₃) δ 1.29 (t, 3H), 1.53 (bd, 1H), 1.94 (bd, 2H), 2.01 (bd, 1H), 2.50 (q, 2H), 2.79 (bd, 2H), 3.83 (bs, 2H), 3.88 (bd, 2H), 6.83 (d, 1H), 7.16 (t, 1H), 7.33 (m, 2H), 7.82 (d, 1H), 8.55 (d, 1H), 8.86 (d, 1H), 11.08 (s, 1H), 12.99 (s, 1H).

In essentially the same manner the following compounds were obtained from the corresponding starting materials:

5-(2-Piperidin-1-yl-benzyloxy)-2-propionylamino-benzoic acid
5-(2-Piperidin-1-yl-phenoxymethyl)-2-propionylamino-benzoic acid
5-(2-Piperidin-1-yl-phenylsulfanylmethyl)-2-propionylamino-benzoic acid
5-[(E)-2-(2-Piperidin-1-yl-phenyl)-vinyl]-2-propionylamino-benzoic acid
5-(2-Piperidin-1-yl-phenylsulfanyl)-2-propionylamino-benzoic acid
5-(2-Morpholin-4-yl-benzyloxy)-2-propionylamino-benzoic acid
5-(2-Morpholin-4-yl-phenoxymethyl)-2-propionylamino-benzoic acid
5-(2-Morpholin-4-yl-phenylsulfanylmethyl)-2-propionylamino-benzoic acid
5-(2-Morpholin-4-yl-phenoxy)-2-propionylamino-benzoic acid ¹H NMR (CDCl3) δ 1.29 (t, 3H), 2.49 (q, 2H), 3.17 (bs, 4H), 3.88 (bs, 4H), 6.94 (d, 1H), 7.06 (t, 1H), 7.11 (d, 1H), 7.18 (m, 2H), 7.67 (d, 1H), 8.71 (d, 1H), 10.08 (bs, 1H).

5-(2-Morpholin-4-yl-phenylsulfanyl)-2-propionylamino-benzoic acid
5-[(E)-2-(2-Morpholin-4-yl-phenyl)-vinyl]-2-propionylamino-benzoic acid
5-{(E)-2-[2-(4-Methyl-piperazin-1-yl)-phenyl]-vinyl}-2-propionylamino-benzoic acid
5-[2-(4-Methyl-piperazin-1-yl)-benzyloxy]-2-propionylamino-benzoic acid
5-[2-(4-Methyl-piperazin-1-yl)-phenoxymethyl]-2-propionylamino-benzoic acid
5-[2-(4-Methyl-piperazin-1-yl)-phenylsulfanylmethyl]-2-propionylamino-benzoic acid
5-[2-(4-Methyl-piperazin-1-yl)-phenoxy]-2-propionylamino-benzoic acid
5-[2-(4-Methyl-piperazin-1-yl)-phenylsulfanyl]-2-propionylamino-benzoic acid

EXAMPLE 6

5-(2-Phenoxy-phenoxy)-2-propionylamino-benzoic Acid

A mixture of 5-hydroxy-2-propionylamino-benzoic acid methyl ester (2.2 g, 10 mmol), (2-phenoxy)phenylboronic acid (4.3 g, 20 mmol), anhydrous copper(II) acetate (1.8 g, 10 mmol) and pyridine (4.0 g, 50 mmol) in CH₂Cl₂ (50 mL) was stirred at room temperature for 72 h in the presence of 5 Å powdered molecular sieves. The reaction mixture was then filtered through Celite and chromatographed on silica gel (R_f=0.11, CH₂Cl₂) to give the intermediate methyl ester. This was dissolved in a mixture of methanol (5 mL) and 1M NaOH (5 mL), warmed at 60° C. for 1 h, and then acidified to pH 3 with 1 M HCl. After cooling, the pure title compound was collected by filtration, dried, and obtained as a grey solid (0.34 g, 9% yield).

¹H NMR (CDCl₃) δ 1.27 (t, 3H), 2.48 (q, 2H), 6.90 (d, 2 H), 7.03–7.10 (m, 3H), 7.11–7.19 (m, 3H), 7.28 (t, 2H), 7.64 (d, 1H) 8.69 (d, 1H), 10.7 (bs, 1H).

In essentially the same manner the following compounds were obtained from the corresponding starting materials:

2-Propionylamino-5-(3-trifluoromethyl-phenoxy)-benzoic Acid

¹H NMR (CD₃OD) δ 1.25 (t, 3H), 2.48 (q, 2H), 7.22 (d, 1 H), 7.26 (s, 1H), 7.30 (dd, 1H), 7.42 (d, 1H), 7.56 (t, 1H), 7.72 (d, 1H), 8.63 (d, 1H).

2-Propionylamino-5-(2-trifluoromethyl-phenylamino)-benzoic Acid

¹H NMR (CDCl₃) δ 1.29 (t, 3H), 2.50 (q, 2H), 6.04 (bs, 1 H), 6.96 (t, 1H), 7.19 (d, 1H), 7.38 (t, 1H), 7.41 (dd, 1H), 7.58 (d, 1H), 7.85 (d, 1H), 8.74 (d, 1H), 10.8 (bs, 1H).

2-Propionylamino-5-(2-trifluoromethyl-phenoxy)-benzoic Acid

¹H NMR (CDCl₃) δ 1.28 (t, 3H), 2.50 (q, 2H), 6.89 (d, 1 H), 7.19 (t, 1H), 7.30 (dd, 1H), 7.47 (t, 1H), 7.69 (d, 1H), 7.79 (d, 1H), 8.78 (d, 1H), 10.8 (bs, 1H).

5-(Biphenyl-2-yloxy)-2-propionylamino-benzoic Acid

¹H NMR (CDCl₃) δ 1.27 (t, 3H), 2.48 (q, 2H), 6.98 (d, 1H), 7.18 (dd, 1H), 7.22–7.40 (m, 5H), 7.47 (dd, 1H), 7.53(d, 2H), 7.66 (d, 1H), 8.67 (d, 1H), 10.8 (bs, 1H).

2-(Cyclopropanecarbonyl-amino)-5-(2-trifluoromethyl-phenoxy)-benzoic Acid

¹H NMR (CDCl₃) δ 0.87 (m, 2H), 1.09 (m, 2H), 1.62 (m, 1H), 6.86 (d, 1 H), 7.15 (t, 1H), 7,23 (dd, 1H), 7.44 (t, 1H), 7.67 (d, 1H), 7.76 (d, 1H), 8,70 (d, 1H), 11.3 (bs, 1H).

5-(3,5-Bis-trifluoromethyl-phenoxy)-2-(cyclopropanecarbonyl-amino)-benzoic Acid

¹H NMR (CDCl₃) δ 0.88 (m, 2H), 1.08 (m, 2H), 1.63 (m, 1H), 7.24 (dd, 1H), 7.32 (s, 2H), 7.54 (s, 1H), 7.78 (d, 1H), 8.76 (d, 1H), 11.4 (bs, 1H).

2-Propionylamino-5-(2-trifluoromethoxy-phenoxy)-benzoic Acid $^1$H NMR (DMSO-d$_6$) δ 1.13 (t, 3H), 2.41 (q, 2H), 7.14 (d, 1 H), 7.30 (t, 1H), 7.34 (dd, 1H), 7.42 (t, 1H), 7.48 (d, 1H), 7.55 (d, 1H), 8.50 (d, 1H), 11.0 (bs, 1H).

5-(3,5-Bis-trifluoromethyl-phenoxy)-2-propionylamino-benzoic Acid $^1$H NMR (DMSO-d$_6$) δ 1.12 (t, 3H), 2.41 (q, 2H), 7.47 (dd, 1H), 7.63 (s, 2H), 7.68 (d, 1H), 7.85 (s, 1H), 8.55 (d, 1H), 11.05 (bs, 1H).

2-Propionylamino-5-(2-trifluoromethoxy-phenylamino)-benzoic Acid $^1$H NMR (CDCl$_3$) δ 1.30 (t, 3H), 2.50 (q, 2H), 5.89 (bs, 1H), 6.86 (m, 1H), 7.15 (d, 2H), 7.25 (d, 1H), 7.38 (dd, 1H), 7.82 (d, 1H), 8.72 (d, 1H), 10.93 (bs, 1H).

EXAMPLE 7

2-(Cyclopropanecarbonyl-amino)-5-(2-trifluoromethyl-benzyloxy)-benzoic Acid

A mixture of 2-(cyclopropanecarbonyl-amino)-5-hydroxy-benzoic acid (7.0 g, 32 mmol) and 2-(trifluoromethyl)-benzyl bromide (9.09 g, 38 mmol) in 0.5 M KOH (158 mL, 79 mmol) and acetone (200 mL) was heated to reflux. After 4 hours, acetone was evaporated and the resulting mixture was diluted with more water and washed with CH$_2$Cl$_2$. The water phase was acidified with 1 M HCl and the resulting solid was collected by filtration. Recrystallisation in methanol gave the product as an off-white powder (6.0 g, yield 50%).

$^1$H NMR (DMSO-d$_6$) δ 0.80–0.87 (m, 4H), 1.66–1.74 (m, 1H), 5.30 (s, 2H), 7.27 (dd, 1 H), 7.52 (d, 1H), 7.59 (t, 1H), 7.73 (t, 1H), 7.77 (d, 1H), 7.81 (d, 1H), 8.33 (d, 1H), 11.1 (bs, 1H). $^{13}$C NMR (DMSO-d$_6$) δ 7.4 (2×CH2), 15.6 (CH), 66.5 (CH2), 115.6 (CH), 118.3 (C), 120.7 (CH), 122.2 (CH), 124.2 (CF3, q, JCF=273.9 Hz), 126.1 (CH, q, JCF=5.5 Hz), 126.8 (C, q, JCF=30.4 Hz), 128.7 (CH), 130.3 (CH), 132.8 (CH), 134.6 (C), 134.7 (C), 152.7 (C), 168.9 (COOH), 171.2 (C=O). MS-ESI: m/z 380 [MH]+.

In essentially the same manner the following compounds were obtained from the corresponding starting materials;

2-(Cyclopropanecarbonyl-amino)-5-(3-trifluoromethyl-benzyloxy)-benzoic Acid $^1$H NMR (DMSO-d$_6$) δ 0.84 (m, 4H), 1.70 (m, 2H), 5.23 (s, 2H), 7.29 (dd, 1H), 7.56 (d, 1H), 7.65 (t, 1H), 7.71 (d, 3H), 7.78 (d, 1H), 7.82 (s, 1H), 8.31 (d, 1H), 10.98 (bs, 1H), 13.62 (bs, 1H).

2-Propionylamino-5-(2-trifluoromethyl-benzyloxy)-benzoic Acid.

$^1$H NMR (DMSO-d$_6$) δ 1.08 (t, 3H), 2.33 (q, 2H), 5.22 (s, 2H), 7.23 (dd, 1H), 7.48 (s, 1H), 7.53 (t, 1H), 7.74 (m, 3H), 8.35 (d, 1H), 10.8 (bs, 1H), 14.1 (bs, 1H).

5-(Biphenyl-2-ylmethoxy)-2-propionylamino-benzoic Acid $^1$H NMR (DMSO-d$_6$) δ 1.08 (t, 3H), 2.20 (q, 2H), 4.92 (s, 2H), 7.10 (dd, 1H), 7.36 (m, 9H), 7.57 (dd, 1H), 8.25 (d, 1H), 10.76 (bs, 1H).

2-Propionylamino-5-(2-trifluoromethoxy-benzyloxy)-benzoic Acid $^1$H NMR (DMSO-d$_6$) δ 1.12 (t, 3H), 2.37 (q, 2H), 5.16 (s, 2H), 7.29 (dd, 1H), 7.44 (t, 2H), 7.52 (dt, 2H), 7.66 (d, 1H), 8.37 (d, 1H), 10.79 (s, 1H).

EXAMPLE 8

2-Propionylamino-5-(3-propylamino-benzyloxy)-benzoic Acid

A mixture of 5-(3-nitro-benzyloxy)-2-propionylamino-benzoic acid methyl ester (196 mg, 0.54 mmol, prepared according to EXAMPLE 7) and hydrazine hydrate (0.81 mL, 1.62 mmol) in 1,2-dichloroethane (15 mL) was cooled to 5° C. Raney-nickel (50 mg) was added carefully in small portions. After the addition the reaction mixture was allowed to reach room temperature and was left with stirring for 2 hours. The catalyst was removed by filtration and the organic phase was washed with water, dried over Na$_2$SO$_4$, filtered and evaporated to dryness. The crude amine, triacetoxy sodium borohydride (241 mg, 1.10 mmol), propionaldehyde (0.54 mL of a 1M solution in 1,2-dichloroethane, 540 mmol) and acetic acid (0.43 mL) were allowed to react in 1,2-dichloroethane at room temperature for 10 minutes. The reaction mixture was filtered through silica gel 60, which was then washed with CHCl$_3$. The solvents were removed by evaporation, which afforded the pure ester product. This was hydrolysed in ethanol (3 mL) and 1M NaOH (1 mL) over night, acidified with 1M HCl until pH 6 and the product was collected by filtration (83 mg, total yield 43%).

$^1$H NMR (DMSO-d$_6$) δ 0.92 (t, 3H), 1.11 (t, 3H), 1.54 (m, 2H), 2.37 (q, 2H), 2.95 (t, 2H), 4.99 (s, 2H), 6.50 (dd, 1H), 6.57 (d, 1H), 6.62 (s, 1H), 7.06 (t, 1H), 7.25 (dd, 1H), 7.51 (d, 1H), 8.36 (d, 1H), 10.83 (s, 1H).

In essentially the same manner the following compound was obtained from the corresponding starting materials:

2-Propionylamino-5-(2-propylamino-benzyloxy)-benzoic Acid $^1$H NMR (DMSO-d$_6$) δ 0.94 (t, 3H), 1.12 (t, 3H), 1.56 (m, 2H), 2.37 (q, 2H), 3.07 (t, 2H), 5.03 (s, 2H), 5.08 (bs, 1H), 6.58 (t, 1H), 6.62 (d, 1H), 7.15 (dt, 1H), 7.22 (dd, 1H), 7.29 (dd, 1H), 7.56 (d, 1H), 8.36 (d, 1H), 10.82 (s, 1H), 13.61 (bs, 1H).

EXAMPLE 9

2-Propionylamino-5-(2-trifluoromethyl-benzylamino)-benzoic Acid

A mixture of 5-amino-2-propionylamino-benzoic acid methyl ester (100 mg, 1.12 mmol), 2-trifluoromethyl benzaldehyde (196 mg, 1.12 mmol), sodium acetate trihydrate (305 mg, 2.24 mmol) and acetic acid (2.7 mL) was stirred at room temperature for 10 minutes in a mixture of methanol (9 mL) and water (7 mL). Sodium cyanoborohydride (98 mg, 1.57 mmol) was added in small portions whereafter the reaction mixture was stirred at room temperature for 30 minutes. The reaction mixture was poured onto water (50 mL) and the aqueous solution was brought to basic pH with 2M NaOH. Cooling the mixture in an ice-bath afforded the pure ester product, which was collected by filtration (330 mg). The ester was hydrolysed in methanol (19 mL) and 5M NaOH (0.5 mL) over night, acidified with 2M HCl and the product was collected by filtration (265 mg, total yield 64%)

$^1$H NMR (DMSO-$d_6$) δ 1.09 (t, 3H), 2.30 (q, 2H), 4.42 (s, 2H), 6.44 (bs, 1H), 6.74 (dd, 1H), 7.12 (d, 1H), 7.37 (t, 1H), 7.62 (m, 2H), 7.77 (d, 1H), 8.11 (d, 1H), 10.54 (bs, 1H), 13.21 (bs, 1H).

In essentially the same manner the following compound was obtained from the corresponding starting materials:

2-Propionylamino-5-(3-trifluoromethyl-benzylamino)-benzoic Acid $^1$H NMR (DMSO-$d_6$) δ 1.09 (t, 3H), 2.30 (q, 2H), 4.36 (s, 2H), 6.41 (bs, 1H), 6.80 (d, 1H), 7.17 (s, 1H), 7.59 (m, 2H), 7.66 (d, 1H), 7.73.(s, 1H), 8.09 (d, 1H), 10.48 (bs, 1H), 13.26 (bs, 1H).

EXAMPLE 10

2-Propionylamino-5-(3-trifluoromethyl-phenoxymethyl)-benzoic Acid

A mixture of 5-bromomethyl-2-propionylamino-benzoic acid methyl ester (250 mg, 0.83 mmol), 3-trifluoromethyl phenol (149 mg, 0.92 mmol) and potassium carbonate (173 mg, 1.25 mmol) was heated at reflux in acetone (6 mL) for 18 hours. The reaction mixture was allowed to reach room temperature and was then poured into water (20 mL) under vigorous stirring. The aqueous mixture was extracted with CHCl$_3$ (40 mL) and the organic layer was dried over Na$_2$SO$_4$, filtered and evaporated to dryness. Chromatography using silica gel 60 and heptane/ethyl acetate (4:1) as eluent afforded the pure ester product (239 mg). This was hydrolysed in ethanol (10 mL) and 1M NaOH (10 mL) over night, acidified with 1M HCl and the product was collected by filtration (215 mg, total yield 71%).

$^1$H NMR (DMSO-$d_6$) δ 1.13 (t, 3H), 2.42 (q, 2H), 5.19 (s, 2H), 7.32 (m, 3H), 7.54 (t, 1H), 7.68 (d, 1H), 8.08 (s, 1H), 8.53 (d, 1H), 11.18 (bs, 1H).

In essentially the same manner the following compounds were obtained from the corresponding starting materials:

5-Phenoxymethyl-2-propionylamino-benzoic Acid $^1$H NMR (DMSO-$d_6$) δ 1.11 (t, 3H), 2.42 (q, 2H), 5.06 (s, 2H), 6.94 (t, 1H), 7.00 (d, 2H), 7.29 (t, 2H), 7.65 (d, 1H), 8.05 (s, 1H), 8.52 (d, 1H), 11.10 (s, 1H), 13.63 (bs, 1H).

2-Propionylamino-5-(2-trifluoromethyl-phenoxymethyl)benzoic Acid $^1$H NMR (DMSO-$d_6$) δ 1.12 (t, 3H), 2.42 (q, 2H), 5.25 (s, 2H), 7.10 (t, 1H), 7.33 (d, 1H), 7.62 (m, 3H), 8.10 (d, 1H), 8.51 (d, 1H), 11.12 (s, 1H), 13.64 (bs, 1H).

2-Propionylamino-5-(2-trifluoromethoxy-phenoxymethyl)-benzoic Acid $^1$H NMR (DMSO-$d_6$) δ 1.13 (t, 3H), 2.42 (q, 2H), 5.21 (s, 2H), 7.04 (t, 1H), 7.31 (d, 1H), 7.36 (m, 2H), 7.63 (d, 1H), 8.09 (s, 1H), 8.52 (d, 1H), 11.22 (bs, 1H).

2-Propionylamino-5-(2-trifluoromethyl-phenylsulfanylmethyl)-benzoic Acid $^1$H NMR (DMSO-$d_6$) δ 1.12 (t, 3H), 2.40 (q, 2H), 4.31 (s, 2H), 7.19 (t, 1H), 7.30 (t, 1h), 7.43 (d, 1H), 7.45 (d, 1H), 8,01 (s, 1H), 8.44 (d, 1H), 11.15 (bs, 1H).

2-Propionylamino-5-(2-trifluoromethoxy-phenylsulfanylmethyl)-benzoic acid

2-Propionylamino-5-(2-propylamino-phenoxymethyl)-benzoic acid 5-(2-Dipropylamino-phenoxymethyl)-2-propionylamino-benzoic acid 2-Propionylamino-5-(3-propylamino-phenoxymethyl)-benzoic acid 5-(3-Dipropylamino-phenoxymethyl)-2-propionylamino-benzoic acid 2-Propionylamino-5-(2-propylamino-phenylsulfanylmethyl)-benzoic acid 5-(2-Dipropylamino-phenylsulfanylmethyl)-2-propionylamino-benzoic acid 2-Propionylamino-5-(3-propylamino-phenylsulfanylmethyl)-benzoic acid 5-(3-Dipropylamino-phenylsulfanylmethyl)-2-propionylamino-benzoic acid

EXAMPLE 11

5-[(E)-2-(2-Fluoro-phenyl)-vinyl]-2-propionylamino-benzoic Acid (Not Included in the Claims)

To a mixture of 5-bromo-2-propionylamino-benzoic acid methyl ester (1.0 g, 3.50 mmol), potassium carbonate (532 mg, 3.85 mmol), tri-n-butyl amine (0.917 mL, 3.85 mmol) and PdCl$_2$(PPh$_3$)$_2$ (35 mg, 0.05 mmol) in DMF (20 mL) was added 2-fluoro-styrene (0.50 mL, 4.2 mmol). The reaction mixture was heated to 150° C. and left at this temperature for 18 hours. after which it was allowed to reach room temperature. Water (10 mL) and 5M NaOH (2 mL) were added and the temperature was once again raised to 150° C. After one hour at this temperature the reaction mixture was allowed to reach room temperature. Water (50 mL) was added and the mixture was filtered by suction through Celite. The filtrate was acidified with 5M HCl, the product collected by filtration and re-crystallised from ethanol (511 mg, 47%).

$^1$H NMR (DMSO-$d_6$) δ 1.13 (t, 3H), 2.42 (q, 2H), 7.26 (m, 5H), 7.79 (t, 1H), 7.89 (d, 1H), 8,14 (s, 1H), 8.53 (d, 1H), 11.18 (bs, 1H).

In essentially the same manner the following compounds were obtained from the corresponding starting materials:

2-Propionylamino-5-((E)-styryl)-benzoic Acid $^1$H NMR (DMSO-$d_6$) δ 1.12 (t, 3H), 2.38 (q, 2H), 7.28 (m, 3H), 7.36 (t, 2H), 7.59 (d, 2H), 7.85 (d, 2H), 8,14 (s, 1H), 8.52 (d, 1H), 11.13 (s, 1H).

2-Propionylamino-5- [(E)-2-(2-trifluoromethyl-phenyl)-vinyl]-benzoic Acid $^1$H NMR (DMSO-$d_6$) δ 1.11 (t, 3H), 2.43 (q, 2H), 7.32 (m, 2H), 7.48 (t, 1H), 7.70 (t, 1H), 7.75 (d, 1H), 7.85 (dd, 1H), 8.00 (d, 1H), 8.18 (d, 1H), 8.58 (d, 1H), 11.16 (bs, 1H).

2-Propionylamino-5-[(E)-2-(3-trifluoromethyl-phenyl)-vinyl]-benzoic Acid $^1$H NMR (DMSO-d$_6$) δ 1.12 (t, 3H), 2.41 (q, 2H), 7.32 (d, 1H), 7.46 (d, 1H), 7.59 (d, 2H), 7.87 (m, 2H), 7.96 (s, 1H), 8.22 (d, 1H), 8.54 (d, 1H), 11.21 (bs, 1H).

2-Propionylamino-5-[(E)-2-(2-trifluoromethoxy-phenyl)-vinyl]-benzoic acid

2-Propionylamino-5-[(E)-2-(3-trifluoromethoxy-phenyl)-vinyl]-benzoic acid

EXAMPLE 12

5-Phenylethynyl-2-propionylamino-benzoic Acid

To a solution of 5-bromo-2-propionylamino-benzoic acid methyl ester (2.0 g, 7.0 mmol) in diethyl amine (55 mL) was added PdCl$_2$(PPb$_3$)$_2$ (708 mg, 0.49 mmol), phenyl acetylene (2.21 mL, 20.1 mmol) and copper (I) iodide (109 mg, 0.27 mmol). The reaction mixture was heated to 50° C. and was left with stirring at this temperature for 18 hours. After having been allowed to reach room temperature the reaction mixture was divided between ethyl acetate and water. The organic layer was washed with brine, dried over MgSO$_4$, filtered and evaporated to dryness. Chromatography using silica gel 60 and heptane/ethyl acetate (3:1) as eluent afforded an orange-coloured crude product to which was added ethanol (50 mL). The suspension was brought to boiling, filtered hot and the filtrate was allowed to slowly reach room temperature. The precipitated grey material was collected by filtration and washed with ethanol to yield the pure ester product (1.20 g). A portion of this (400 mg) was hydrolysed in ethanol (10 mL) and 1M NaOH (10 mL) over night, acidified with 1M HCl and the product was collected by filtration (362 mg, total yield 53%).

$^1$H NMR (DMSO-d$_6$) δ 1.12 (t, 3H), 2.45 (q, 2H), 7.44 (m, 3H), 7.58 (m, 2H), 7.76 (dd, 1H), 8.12 (d, 1H), 8.60 (d, 1H), 11.24 (bs, 1H), 13.96 (bs, 1H).

In essentially the same manner the following compounds were obtained from the corresponding starting materials:

2-Propionylamino-5-(2-trifluoromethoxy-phenylethynyl)-benzoic acid

2-Propionylamino-5-(3-trifluoromethoxy-phenylethynyl)-benzoic acid

2-Propionylamino-5-(2-trifluoromethyl-phenylethynyl)-benzoic acid

2-Propionylamino-5-(3-trifluoromethyl-phenylethynyl)-benzoic acid

EXAMPLE 13

5-Benzyl-2-propionylamino-benzoic Acid

Methyl anthranilate (30.9 g; 205 mmols) and benzyl alcohol (4.43 g; 40,9 mmols) were dissolved in 50 mL of p-xylene. Montmorillonite (1.3 g), activated with hydrochloric acid, was added to the reaction mixture, which was then heated to boiling. The water produced during the reaction was collected using a Dean-Starck-apparatus. After three hours the solvent and the excess of methyl anthranilate were distilled off at reduced pressure. Chromatography using silica gel 60 and heptane/ethyl acetate (19/1->9/1) as eluent afforded 430 mg (4.4%) of the desired methyl 5-benzylanthranilate.

Methyl 5-benzylanthranilate (300 mg; 1.24 mmols) was dissolved in 7 mL of chloroform and propionyl chloride (344 mg; 3.72 mmols) was added and the reaction mixture was left at room temperature for 18 hours. Aqueous saturated sodium bicarbonate (5 mL) was added to the reaction mixture whereafter the organic phase was separated, dried over magnesium sulphate, filtered and evaporated to dryness. The resulting yellow oil was dissolved in 5 mL of methanol and aqueous sodium hydroxide (1M, 5 mL) was added. The reaction mixture was then heated to 60° C. for two hours. After cooling to room-temperature the reaction mixture was acidified with 20 mL of hydrochloric acid (1M). The white precipitate was filtered with suction, washed twice with water and dried under vacuum yielding the title compound quantitatively. $^1$H NMR (DMSO-d$_6$) δ 1.09 (t, 3H, J=7.4, —CH3), 2.37 (q, 2H, J=7.5, —CH2—CH3), 3.92 (s, 2H, —CH2-Ph), 7.13–7.45 (m, 5H, -Ph), 7.44 (d, 1H, J=8.6, H4), 7.79 (s, 1H, H6), 8.39 (d, 1H, J=8.5, H3), 11.01 (s, 1H, >NH), 13.54 (bs, 1H, —COOH).

EXAMPLE 14

5-Hydroxy-2-propionylamino-benzoic Acid Methyl Ester

5-Hydroxy isatoic anhydride (17.9 g, 0.1 mol) was heated to reflux with sodium methoxide (0.5 g, 0.01 mol) in methanol (600 mL) for 1 h. The reaction mixture was cooled on icebath, propionic anhydride (15.0 g, 0.115 mol) was added and then the mixture was heated to reflux for 0.5 h The mixture was then concentrated under reduced pressure to app. one-half of its original volume and left over night in a refrigerator. The resulting precipitate was collected, washed with methanol and dried to give the title compound as pure white crystals (15.2 g, 0.068 mol).

$^1$H NMR (DMSO-d$_6$) δ 1.08 (t, 3H), 2.31 (q, 2H), 3.80 (s, 3 H), 6.98 (dd, 1H), 7.25 (d, 1H), 7.93 (d, 1H), 9.6 (bs, 1H), 10.1 (bs, 1H).

EXAMPLE 15

5-Amino-2-(cyclopropanecarbonyl-amino)-benzoic Acid Methyl Ester 5-nitroisatoic anhydride (20.8 g, 0.1 mol) ) was heated to reflux with sodium methoxide (0.5 g, 0.01 mol) in methanol (600 mL). After 1 h, the solvent was evaporated under vacuum and the residue dissolved in 1,2-dichloroethane (400 mL), washed with cold water and dried over MgSO$_4$. Cyclopropanecarbonyl chloride (20.9 g, 0.2 mol) was added to the solution and then heated at 80° C. for 4.5 h. The mixture was allowed to cool and water (200 mL) was added under vigorous stirring. After 0.5 h, the stirring was interrupted and the phases separated, the C$_2$H$_4$Cl$_2$ layer washed with sodium bicarbonate solution and dried over MgSO$_4$. Evaporation of the solvent afforded 2-(cyclopropanecarbonyl-amino)-5-nitro-benzoic acid methyl ester (21.7 g, 0.082 mmol). This material was dissolved in methanol (500 mL) and 10% Pd/C (2.2 g) was added. The flask was then flushed with H$_2$ and stirred at room temperature and at 1 atm. After 5 h reduction, the catalyst was removed by filtration through Celite. The catalyst was carefully washed and the combined filtrate evaporated to dryness to give the pure title compound as a grey solid (18.0 g, 0.077 mol).

$^1$H NMR (CDCl$_3$+CD$_3$OD) δ 0.84 (m, 2H), 1.06 (m, 2H), 1.60 (m, 1H), 3.91 (s, 3H), 6.89 (dd, 1H), 7.33 (d, 1H), 8.47 (d, 1H), 10.9 (bs, 1H).

In essentially the same manner the following compound was obtained from the corresponding starting materials:

5-Amino-2-propionylamino-benzoic Acid Methyl Ester $^1$H NMR (CDCl$_3$) δ 1.27 (t, 3H), 2.45 (q, 2H), 3.64 (bs, 2H), 3.91 (s, 3H), 6.92 (dd, 1H), 7.34 (d, 1H), 8.53 (d, 1H), 10.7 (bs, 1H).

EXAMPLE 16

2-(Cyclopropanecarbonyl-amino)-5-hydroxy-benzoic Acid

2-Amino-5-hydroxy-benzoic acid (15.3 g, 0.1 mol) was dissolved in 0.5 M NaOH (650 mL, 0.325 mol). Toluene (300 mL) was added and the mixture was cooled to 4° C. Cyclopropanecarbonyl chloride (26.1 g, 0.25 mol) was added in portions under vigorous stirring and the stirring continued for about 10 minutes. The partly diacylated product precipitated on addition of 5 M HCl and was collected by filtration. Hydrolysis by stirring in 5 M NaOH (150 mL) for 1 hour at room temperature, cooling to 4° C. and acidification with 2.5 M HCl gave after filtration and drying a light purpur solid (19 g, yield 86%).

$^1$H NMR (DMSO-d$_6$) δ 0.73–0.79 (m, 4H), 1.59–1.64 (m, 1H), 6.90 (dd, 1H), 7.31 (d, 1H), 8.12 (d, 1H), 9.5 (bs, 1H), 10.9 (bs, 1H).

EXAMPLE 17

5-(2-Amino-phenylsulfanyl)-2-propionylaminobenzoic Acid Methyl Ester

A mixture of 5-(2-nitro-phenylsulfanyl)-2-propionylamino-benzoic acid methyl ester (110 mg, 0.31 mmol, prepared according to Sevbo et al. 1976) and palladium-on-charcoal (10%, 25 mg) in ethyl acetate (5 mL) was stirred in an atmosphere of hydrogen (1 atm) at room temperature for 2 hours. The catalyst was filtered off and the solvent was removed by evaporation to yield the title compound quantitatively.

$^1$H NMR (CDCl$_3$) δ 1.28 (t, 3H), 2.47 (q, 2H), 3.93 (s, 3H), 4.28 (bs, 2H), 6.80 (m, 2H), 7.25 (m, 2H), 7.45 (d, 1H), 7.90 (d, 1H), 9.24 (d, 1H), 10.97 (bs, 1H).

EXAMPLE 18

5-Bromomethyl-2-propionylamino-benzoic Acid Methyl Ester

2-Amino-5-methyl-benzoic acid (23,58 g, 156 mmol) was dissolved in methanol. The solution was brought to 0° C. on an ice-bath and thionyl chloride (46.3 mL, 636 mmol) was added dropwise during 30 minutes. After the addition the reaction mixture was refluxed for 18 hours and was then allowed to reach room temperature. The solvent was evaporated and the remainder was divided between CH$_2$Cl$_2$ (500 mL) and aqueous saturated NaHCO$_3$ (500 mL). The organic layer was washed with an additional 500 mL of aqueous saturated NaHCO$_3$, dried over MgSO$_4$ and evaporated to dryness (16.59 g, 64%).

2-Amino-5-methyl-benzoic acid methyl ester (8.00 g, 48.4 mmol) was dissolved in CHCl$_3$ (275 mL) and propionyl chloride (12,6 mL, 145 mmol) was added dropwise during 10 minutes after which the reaction mixture was left with stirring at room temperature for 72 hours.

Aqueous saturated NaHCO$_3$ (400 mL) was carefully added under vigorous stirring and when no more gas evolved the organic layer was separated, dried over MgSO4, filtered and evaporated to dryness (10.06 g, 94%).

The radical bromination was performed as described by Patil et al. 1989: 5-Methyl-2-propionylamino-benzoic acid methyl ester (8.85 g, 40 mmol) and 1,3-dibromo-5,5-dimethyl hydantoin (DDH) (5,72 g, 20 mmol) in a mixture of CHCl$_3$ (500 mL) and CCl$_4$ (500 mL) was heated to reflux. Every 60 minutes 50 mg of dibenzoyl peroxide was added for six hours and then the reaction mixture was left at reflux over night. It was then allowed to reach room temperature and the solvents were removed by evaporation. Chromatography using silica gel 60 and heptane/ethyl acetate (18:2 ->17:3 ->16:4) as eluent afforded the pure title compound (6.40 g, 53%).

$^1$H NMR (CDCl$_3$) δ 1.26 (t, 3H), 2.48 (q, 2H), 3.95 (s, 3H), 4.47 (s, 2H), 7.55 (dd, 1H), 8.04 (d, 1H), 8.72 (d, 1H), 11.06 (bs, 1H).

EXAMPLE 19

5-Bromo-2-propionylamino-benzoic Acid Methyl Ester

2-Amino-5-bromo-benzoic acid methyl ester (6.37 g, 27.7 mmol) was dissolved in CHCl$_3$ (140 mL) and propionyl chloride (4.81 mnL, 55.4 mmol) was added dropwise during 10 minutes and the reaction mixture was left at room temperature over night. Aqueous saturated NaHCO$_3$ (150 mL) was added carefully and the mixture was left with vigorous stirring for 2 hours. The organic layer was separated, dried over MgSO$_4$, filtered and evaporated to dryness (7.54 g, 95%).

$^1$H NMR (CDCl$_3$) δ 1.26 (t, 3H), 2.42 (q, 2H), 3.91 (s, 3H), 7.62 (dd, 1H), 8.13 (d, 1H), 8.67 (d, 1H), 11.02 (bs, 1H).

Pharmacological Methods

Inhibition Assay of DHODH Activity

Inhibition of recombinant human DHODH was assayed by the dihydroorotate (DHO) driven reduction of dichloroindophenol (DCIP), (Bruneau et al., 1998). The standard assay mixture contained 0.4 μg/mL recombinant protein, 50 mM Tris pH8, 100 μM decylubiquinone, 1 mM KCN, 200 μM DCIP and 0.1% Triton X-100. Inhibitory compounds were added at 10 different concentrations and the enzyme reaction initiated by the addition of 500 μM DHO. The reaction was allowed to continue for 10 minutes before the reduction of DCIP was measured in a microtiterplate reader as a decrease in absorbance at 650 nm. The IC$_{50}$ values (concentration of inhibitor required for 50% inhibition) for each compound were calculated from the obtained dose response curves.

Inhibition of T-cell Proliferation

Inhibition of T cell proliferation was studied in a functional assay. A human T lymphoblast cell line (Jurkat) was cultured in the presence and absence of DHODH inhibiting compounds. Jurkat cells were seeded in microtiterplates at a concentration of 5×10$^5$/mL in RPMI 1640 growth media supplemented with ultraglutamin, 10% fetal calf serum, 1 mM sodium pyruvat, 10 mM HEPES and 0.1 mg/mL gentamycin. A dilution series of ten different concentrations of inhibitor was added to the wells and the plates were kept in a cell incubator for 3 days. At the beginning of the last 4 hours period, the cultures were pulsed with 10 μl/well 0.1Ci/mmol $^3$H-TdR and then harvested on filter papers and counted with a β-counter. The IC$_{50}$ values for each compound were calculated from the obtained dose response curves. Adding 50 μM uridine to the wells monitored the specificity for the mechanism. This reverses the antiproliferative effect by bypassing the DHODH enzyme using an external source of pyrimidine.

Inhibition of Transplant Rejection in the Rat

Inbred rat strains, male PVG (RT1$^c$) (100–149 g) and DA (RT1$^{av1}$) (180–240 g) rats were used as donors and recipients, respectively. Heterotopic cardiac transplantation was performed with a non-suture cuff technique. The donor heart was transplanted to the recipient's right vessels of the neck the aortic root being anastomosed to the common carotid artery and the pulmonary artery to the jugular vein. The graft veins were ligated. Graft survival was monitored twice daily and rejection was defined as cessation of palpable cardiac graft beats. Parallel subgroups of recipients were treated orally with a gastric feeding catheter once daily for ten consecutive days. First day of treatment was the day of transplantation and the rats were treated a few minutes before transplantation.

Determization of Pharmacokinetic Properties in the Mouse

Female mice (SJL/N Tac) were given a single intravenous or oral dose of a mixture of 4 or 6 compounds per cassette (nominal dose: 1 mg/kg/compound). The test items were formulated in physiological saline/5% Cremophor® to a final concentration of each 0.1 mg/mL. Blood samples were collected from vena cava (terminal bleed) into sodium heparinised tubes. The dose formulations and plasma concentrations of each compound were determined by LC-MS/MS. The pharmacokinetic parameters were determined by non-compartmental analysis using WinNonlin Professional (version 4.0.1).

EP0497740 discloses compounds that are stated to be useful as antihyperproliferative/antiinflammatory and anticancer agents. The compound disclosed as most preferred is 5-(2,5-dimethoxy-benzyloxy)-2-hydroxy-benzoic acid methyl ester. The present inventors found 5-(2,5-dimethoxy-benzyloxy)-2-hydroxy-benzoic acid to be inactive as a DHODH inhibitor.

EP0497740 also discloses the compound 2-acetylamino-5-(2,5-dimethoxy-benzyloxy)-benzoic acid methyl ester. The compound 2-acetylamino-5-(2,5-dimethoxy-benzyloxy)-benzoic acid (hereinafter called compound G) has been tested and found to display only a weak inhibitory effect on T-cell proliferation, see Table 1.

EP0815087 discloses compounds structurally related to compounds of formula (I) that are stated to be useful for the treatment of proliferative and/or inflammatory disorders and cancer, e.g., 2-acetylamino-5-[2-(2,5-dimethoxy-phenyl)-ethyl]-benzoic acid methyl ester. 2-Acetylamino-5-[2-(2, 5dimethoxy-phenyl)-ethyl]-benzoic acid (hereinafter called compound H) been tested and found to display a very weak inhibitory effect on T-cell proliferation, see Table 1. The compound 2-propionylamino-5-[2-(2-trifluoromethyl-phenyl)-ethyl]-benzoic acid (hereinafter called compound J) is included as a reference compound. Compound J displayed a weak antiproliferative effect, see Table 1.

The following compounds are intended to illustrate the DHODH inhibitory effect of the compounds of the present invention:

| compound K | 2-propionylamino-5-(2-trifluoromethyl-benzylamino)-benzoic acid |
| compound L | 2-propionylamino-5-(2-trifluoromethyl-phenoxy)-benzoic acid |
| compound M | 2-propionylamino-5-(2-trifluoromethyl-benzyloxy)-benzoic acid |
| compound N | 2-propionylamino-5-(2-trifluoromethyl-phenoxymethyl)-benzoic acid |
| compound O | 2-propionylamino-5-(2-trifluoromethyl-phenylsulfanyl)-benzoic acid |
| compound P | 2-propionylamino-5-(2-trifluoromethyl-phenylsulfanylmethyl)-benzoic acid |
| compound Q | 2-propionylamino-5-[(E)-2-(2-trifluoromethyl-phenyl-vinyl]-benzoic acid |
| compound R | 2-propionylamino-5-[(E)-2-(3-trifluoromethyl-phenyl-vinyl]-benzoic acid |
| compound S | 5-(3,5-bis-trifluoromethyl-phenoxy)-2-propionylamino-benzoic acid |
| compound T | 2-propionylamino-5-(2-propylamino-phenoxy)-benzoic acid |
| compound U | 2-propionylamino-5-(2-propylamino-benzyloxy)-benzoic acid |
| compound AA | 2-propionylamino-5-(2-propylamino-phenylsulfanyl)-benzoic acid |
| compound AB | 5-(2-dipropylamino-phenoxy)-2-propionylamino-benzioc acid |
| compound AC | 2-propionylamino-5-(2-trifluoromethoxy-benzyloxy)-benzoic acid |
| compound AD | 2-propionylamino-5-(2-trifluoromethoxy-phenoxymethyl)-benzoic acid |
| compound AE | 2-propionylamino-5-(2-trifluoromethoxy-phenylsulfanyl)-benzioc acid |

Inhibition of T cell proliferation was studied in a functional assay. Table 1 exemplifies the invention, without limiting the scope thereof. A human T lymphoblast cell line (Jurkat) was cultured in the presence of the compound to be screened. The IC$_{50}$ value for each compound was calculated from the dose response curve. Adding uridine was used to monitor the specificity of the DHODH mechanism.

TABLE 1

Inhibition of T-cell proliferation in vitro.

| | IC$_{50}$ (μM) |
|---|---|
| Compound G (prior art) | 6.2 |
| Compound H (reference) | 12 |
| Compound J (reference) | 2.9 |
| Compound K (invention) | 0.79 |
| Compound L (invention) | 0.78 |
| Compound M (invention) | 0.33 |
| Compound N (invention) | 0.52 |
| Compound O (invention) | 0.25 |
| Compound P (invention) | 0.21 |
| Compound Q (invention) | 0.11 |
| Compound R (invention) | 0.45 |
| Compound S (invention) | 0.14 |
| Compound T (invention) | 0.24 |
| Compound U (invention) | 0.11 |
| Compound AA (invention) | 0.04 |
| Compound AB (invention) | 0.15 |
| Compound AC (invention) | 0.30 |
| Compound AD (invention) | 0.24 |
| Compound AE (invention) | 0.39 |

In comparison with prior art and reference (not according to the invention) compounds, the compounds of the present invention possess advantageous pharmacokinetic properties and high oral bioavailability. The clearance (CL) and half-life ($t_{1/2}$) of representative compounds in the mouse following i.v. administration are shown in Table 2. Table 2 exemplifies the invention, without limiting the scope thereof.

TABLE 2

Pharmacokinetic properties in the mouse.

| | CL (L/h/kg) | $t_{1/2}$ (h) |
|---|---|---|
| Compound G (prior art) | 0.71 | 0.30 |
| Compound AF[a)] (reference) | 0.97 | 0.29 |
| Compound K (invention) | 0.070 | 2.2 |
| Compound L (invention) | 0.015 | 3.1 |
| Compound M (invention) | 0.11 | 4.9 |
| Compound N (invention) | 0.14 | 1.5 |
| Compound O (invention) | 0.033 | 4.6 |
| Compound AG[b)] (invention) | 0.12 | 10 |
| Compound AH[c)] (invention) | 0.018 | 6.6 |

[a)] 2-Acetylamino-5-phenethyl-benzoic acid
[b)] 2-Propionylamino-5-[(E)-styryl]-benzoic acid
[c)] 5-Benzyl-2-propionylamino-benzoic acid In a heart transplantation model in the rat, hearts were rejected in the control group (N=6) on day 6.5 after transplantation. Following daily treatment for 10 days with 2-(cyclopropanecarbonyl-amino)-5-(2-trifluoromethyl-benzyloxy)-benzoic acid (invention) (N=6) or compound S (N=6) the grafts were accepted and there was a tolerance induced as measured as a median graft survival of more than 100 days.

Pharmaceutically acceptable salts of the compounds of formula (I) can be prepared by reacting the free acid with a base in water or in an organic solvent. Lists of suitable salts are found in Remington's Pharmaceutical Sciences, 17.th edition, Mack Publishing Company, Easton, Pa., 1985, p. 1418. Effective quantities of the compounds of this invention are preferably administered to a patient in need of such treatment according to usual routes of administration and formulated in usual pharmaceutical compositions comprising an effective amount of the active ingredient and a suitable pharmaceutically acceptable carrier. Such compositions may take a variety of forms, e.g., solutions, suspensions, emulsions, tablets, capsules, and powders prepared for oral administration, sterile solutions for parental administration, and suppositories for rectal administration or suitable topical formulations. Conventional procedures for the selection and preparation of suitable pharmaceutical formulations are described, for example, in "Pharmaceuticals—The Science of Dosage Form Design", M. B. Aulton, Churchill Livingstone, 1988.

A suitable daily dose for use in the treatment of a disease selected from autoimmune diseases, inflammatory diseases, organ transplant rejection and malignant neoplasia is contemplated to vary between 0.005 mg/kg to about 10 mg/kg body weight, in particular between 0.025 mg/kg to 2 mg/kg body weight, depending upon the specific condition to be treated, the age and weight of the specific patient, and the specific patient's response to the medication. The exact individual dosage, as well as the daily dosage, will be determined according to standard medical principles under the direction of a physician.

REFERENCES

Batt, D G, Inhibitors of dihydroorotate dehydrogenase. Exp. Opin. Ther. Patents, 1999, 9 (1):41–54.
Breedveld F C, New insights in the pathogenesis of rheumatoid arthritis. J. Rheumatol. Suppl., 1998, 53:3–7. Review.
Bruneau J M, Yea C M, Spinella-Jaegle S, Fudali C, Woodward K, Robson P A., Sautes C, Westwood R, Kuo E A, Williamson R A, Ruuth E, Purification of human dihydroorotate dehydrogenase and its inhibition by A77 1726, the active metabolite of leflunomide. Biochem. J., 1998, 336 (Pt 2):299–303.
Chan D M T, Monaco K L, Wang Ru-Ping, Winters M P, New N- and O-arylation with phenylboronic acids and cupric acetate, Tetrahedron Letters, 1998, 39(19):2933–2936.
Cherwinski H M, Cohn R G, Cheung P. Webster D J, Xu Y Z, Caulfield J P, Young J M, Nakano G, Ransom J T, The immunosuppressant leflunomide inhibits lymphocyte proliferation by inhibiting pyrimidine biosynthesis, J. Pharmacol. Exp. Ther., 1995, 275(2):1043–9.
Freitag, D., DE 2064305(A1) 1970.
Gennari M, Negre M, Ambrosoli R, Andreoni V, Vincenti M, Acquati A, Anaerobic Degradation of Acifluorfen by Different Enrichment Cultures. J. Agricultural and Food Chemistry, 1994, 42(5):1232–6.
Hutchinson J H. Cook J J, Brashear K M, Breslin M J, Glass J D, Gould R J, Halczenko W, Holahan M A, Lynch R J, Sitko G R, Stranieri M T, Hartman G D. Non-Peptide Glycoprotein IIb/IIIa Antagonists. 11. Design and in Vivo Evaluation of 3,4-Dihydro-1(1H)-isoquinolinone-Based Antagonists and Ethyl Ester Prodrugs. J. Med. Chem., 1996, 39:4583–91.
Kubinyi, H. Chapter 3. Parameters. In Methods and Principles in Medicinal Chemistry Vol 1, QSAR: Hansch Analysis and Related Approaches; Mannhold, R., Kroogsgard-Larsen, P., Timmermann, H., Eds.; VCH: Weinheim, 1993; pp 21–27.
Mathis C A, Wang Y, Holt D P, Huang G F, Debnath M L, Klunk W E, Synthesis and evaluation of 11C-labeled 6-substituted 2-arylbenzothiazoles as amyloid imaging agents. J. Med. Chem., 2003, 46(13): 2740–54.
Patil S D, Jones C, Nair M G, Galivan J, Maley F, Kisliuk R L, Gaumont Y, Duch D, Ferone R, Folate Analogues. 32. Synthesis and Biological Evaluation of 2-Desamino-2-methyl-N10-propargyl-5,8-dideazafolic Acid and Related Compounds. J. Med. Chem., 1989, 32:1284–89.
Research Disclosure, 1998, 409(May), P561–P562 (No. 40953)
Sevbo D P, Ginzburg O F, 2-Amino-3-phenothiazone derivatives. III. Methyl 2-amino-3-phenothiazone-1-carboxyla Zhurnal Organicheskoi Khimii, 1976, 12(8):1819–25.
Staiger R P and Miller E B, Isatoic anhydride. IV. Reactions with various nucleophiles J. Org. Chem., 1959, 24:1214–1219.

We claim:
1. A compound of formula (I)

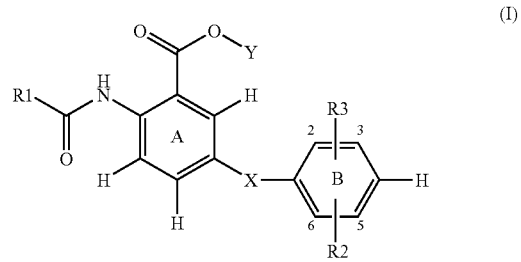

wherein
X is $CH_2$, NH, O, S, CH═CH, C≡C, $NHCH_2$ or $OCH_2$ wherein the nitrogen or oxygen atom is bound to ring A; $CH_2O$ or $CH_2S$ wherein the oxygen or sulphur atom is bound to ring B;

Y is hydrogen, straight or branched $C_1$–$C_4$ alkyl or a pharmaceutically acceptable inorganic cation;

$R_1$ is ethyl or cyclopropyl;

$R_2$ and $R_3$ are the same or different and represent hydrogen, straight or branched $C_1$–$C_4$, alkylthio, $NHR_4$, $NR_4R_5$, trifluoromethyl, trifluoromethoxy, $NHCOR_6$, phenyl, phenoxy, phenylthio or phenylamino; wherein the phenyl moiety optionally is monosubstituted with fluoro;

$R_4$ and $R_5$ independently are hydrogen or straight or branched $C_1$–$C_4$ alkyl; or $R_4$ and $R_5$ together with the nitrogen to which they are bound, form a 5- or 6-membered ring

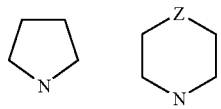

Z is $CH_2$, O, NH or $NCH_3$; and $R_6$ is $C_1$–$C_3$ alkyl, phenylamino, or phenyl optionally mono-substituted with $C_1$–$C_2$ alkoxy or fluoro;

with the proviso that $R_2$ and $R_3$ are not both hydrogen when X is $OCH_2$.

2. A compound according to claim 1 wherein
X is $CH_2$, O, S, CH=CH, $OCH_2$, $CH_2O$ or $CH_2S$;
Y is hydrogen, straight or branched C1–C4 alkyl or a pharmaceutically acceptable inorganic cation;
$R_2$ and $R_3$ are the same or different and represent hydrogen or substituents in the 2-, 3- or 5-positions, selected from $NHR_4$, $NR_4R_5$, trifluoromethyl, trifluoromethoxy, phenyl, phenoxy, phenylthio and phenylamino; wherein the phenyl moiety optionally is monosubstituted with fluoro; and
$R_4$ and $R_5$ independently are hydrogen or straight or branched $C_1$–$C_4$ alkyl.

3. A compound according to claim 1 wherein
X is O, S, $OCH_2$, $CH_2O$ or $CH_2S$;
Y is hydrogen or a pharmaceutically acceptable inorganic cation;
$R_2$ is a substituent in the 2- or 3-position and is $NHR_4$, $NR_4R_5$, trifluoromethyl or trifluoromethoxy;
$R_3$ is hydrogen; and
$R_4$ and $R_5$ independently are hydrogen or straight or branched $C_1$–$C_4$ alkyl.

4. A compound according to claim 1 wherein
X is O, S, $OCH_2$, $CH_2O$ or $CH_2S$;
Y is hydrogen or a pharmaceutically acceptable inorganic cation;
$R_2$ is a substituent in the 2-position and is n-propylamino, di-(n-propyl) amino, trifluoromethyl or trifluoromethoxy; and
$R_3$ is hydrogen.

5. A compound according to claim 1 wherein
X is $OCH_2$; Y is hydrogen or a pharmaceutically acceptable inorganic cation;
$R_2$ is a substituent in the 2-position and is trifluoromethyl; and
$R_3$ is hydrogen.

6. A compound according to claim 1 wherein
X is O;
Y is hydrogen or a pharmaceutically acceptable inorganic cation; and
$R_2$ and $R_3$ are substituents in the 3- and 5-positions, and are trifluoromethyl.

7. A compound according to claim 1 selected from 2-(cyclopropanecarbonyl-amino)-5-(2-trifluoromethyl-benzyloxy)-benzoic acid;
2-propionylamino-5-(2-trifluoromethyl-benzyloxy)-benzoic acid;
5-(3,5-bis-trifluoromethyl-phenoxy)-2-cyclopropanecarbonylamino-benzoic acid; and
5-(3,5-bis-trifluoromethyl-phenoxy)-2-propionylamino-benzoic acid and salts thereof with a pharmaceutically acceptable inorganic cation.

8. A pharmaceutical composition comprising a compound according to claim 1 as an active ingredient, in association with pharmaceutically acceptable excipients.

9. The pharmaceutical composition according to claim 8 wherein the active ingredient is present in an amount so as to give a daily dosage of from 0.005 mg/kg to 10 mg/kg body weight.

10. The pharmaceutical composition according to claim 8 wherein the active ingredient is present in an amount so as to give a daily dosage of from 0.025 mg/kg to 2 mg/kg body weight.

11. The pharmaceutical composition according to claim 8 in the form of a solution, suspension, emulsions, tablet, capsule, or powder for oral administration, a sterile solution for parental administration, a suppository for rectal administration or a topical formulation.

12. A method "of treating a disorder or condition selected from the group consisting of acute and chronic inflammation, rheumatoid arthritis, and transplant rejection in a mammal, comprising administering to the mammal in need of such treatment a therapeutically effective amount of a compound according to claim 1."

13. The compound of claim 1 wherein X is O or $OCH_2$ wherein the oxygen atom is bound to ring A, or $CH_2O$ wherein the oxygen atom is bound to ring B;
Y is hydrogen or a pharmaceutically acceptable inorganic cation;
$R_1$ is ethyl or cyclopropyl; and
$R_2$ and $R_3$ are the same or different and represent hydrogen, trifluoromethyl or trifluoromethoxy, with the proviso that $R_2$ and $R_3$ are not both hydrogen when X is $OCH_2$.

14. A pharmaceutical composition comprising a compound according to claim 13 in a therapeutically effective amount, together with a pharmaceutically acceptable excipient.

15. A compound of formula I

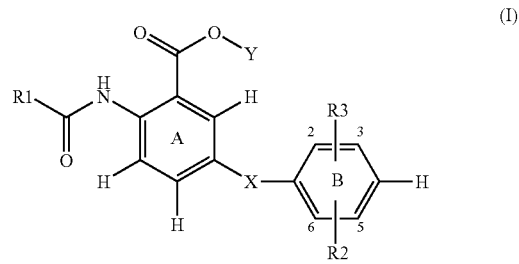

wherein
X is O; $OCH_2$ wherein the oxygen atom is bound to ring A, or $CH_2O$ wherein the oxygen atom is bound to ring B;

Y is hydrogen or a pharmaceutically acceptable inorganic cation;
$R_1$ is ethyl or cyclopropyl;
$R_2$ and $R_3$ are the same or different and represent hydrogen, trifluoromethyl or trifluoromethoxy, with the proviso that $R_2$ and $R_3$ are not both hydrogen.

16. The compound according to claim 15 wherein
X is O;
$R_1$ is ethyl; and
$R_2$ and $R_3$ are substituents in the 3- and 5-positions, and are trifluoromethyl.

17. 5-(3,5-Bis-trifluoromethyl-phenoxy)-2-propionylamino-benzoic acid.

* * * * *

(12) EX PARTE REEXAMINATION CERTIFICATE (6196th)
United States Patent
Jönsson et al.

(10) Number: US 7,074,831 C1
(45) Certificate Issued: Apr. 15, 2008

(54) COMPOUNDS, METHODS FOR THEIR PREPARATION AND USE THEREOF

(75) Inventors: Stig Jönsson, Lund (SE); Gunnar Andersson, Röstånga (SE); Ulf Wellmar, Södra Sandby (SE); Ingela Fritzson, Lund (SE)

(73) Assignee: Active Biotech AB, Lund (SE)

Reexamination Request:
No. 90/008,242, Nov. 9, 2006

Reexamination Certificate for:
Patent No.: 7,074,831
Issued: Jul. 11, 2006
Appl. No.: 11/050,430
Filed: Feb. 4, 2005

(30) Foreign Application Priority Data

Feb. 6, 2004 (SE) ................................. 0400234

(51) Int. Cl.
*A61K 31/192* (2006.01)
*C07C 65/105* (2006.01)

(52) U.S. Cl. ........................ 514/563; 548/435
(58) Field of Classification Search ............... None
See application file for complete search history.

(56) References Cited

FOREIGN PATENT DOCUMENTS

| EP | 0 497 740 A1 | 8/1992 |
|---|---|---|
| WO | WO 96/28430 A1 | 9/1996 |
| WO | WO 03/006425 A2 | 1/2003 |

OTHER PUBLICATIONS

Albert et al., Rainer, "Isoxazolythioamides As Potential Immunosuppressants A Combinatorial Chemistry Approach", *Bioorganic& Medicinal Chemistry Letters*, (1998) vol. 8, No. 16, pp. 2203–2208.

Gennari et al., Mara, "Anaerobic Degradation of Acifluorfen by Different Enrichment Cultures", *J. Agric. Food Chem.*, (1994) vol. 42, No. 5, pp. 1232–1236.

Novartis Forschungsinstitut GmbH, "Synthetic Analogues of Lavendustin A (Novartis Forschungsinstitu GmbH, A–I 230 Vienna, Austria)", *Research Disclosure*, May 10, 1998, vol. 409, No. 053, pp. 40952–40953, Research Disclosure Journal No. 409053.

Database Caplus Chemical Abstracts Service, Columbus, Ohio, US; XP0023303474, Database Accession No. 139:365124.

Sutton et al., Amanda, "The Synthesis of Potentially Selective Inhibitors of Hydroorotate Dehydrogenase. The Utilization of Chemoselective Suzuki Cross–coupling Reactions in a Parallel Synthesis", *Tetrahedron Letters*, (2001) vol. 42, No. 2, pp. 2203–2208.

*Primary Examiner*—Evelyn Mei Huang

(57) ABSTRACT

Compounds of formula (I)

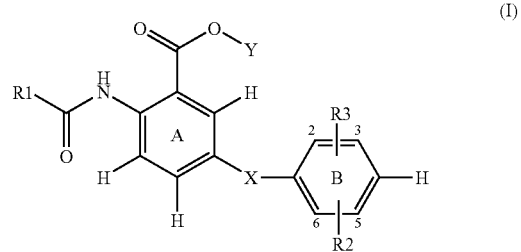

for clinical treatment of autoimmune diseases, inflammatory diseases, organ transplant rejection and malignant neoplasia. A pharmaceutical composition comprising a compound of formula (I) in an amount giving a daily dosage of from 0.005 mg/kg to 10 mg/kg body weight, in particular from 0.025 mg/kg to 2 mg/kg body weight.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 15–17 is confirmed.

Claims 1 and 12 are determined to be patentable as amended.

Claims 2–11 and 13–14, dependent on an amended claim, are determined to be patentable.

1. A compound of formula (I)

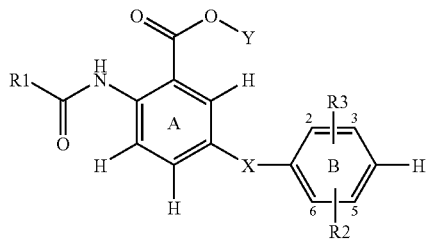

wherein

X is $CH_2$, NH, O, S, CH=CH, C≡C, $NHCH_2$ or $OCH_2$ wherein the nitrogen or oxygen atom is bound to ring A; $CH_2O$ or $CH_2S$ wherein the oxygen or sulphur atom is bound to ring B;

Y is hydrogen, straight or branched $C_1$-$C_4$ alkyl or a pharmaceutically acceptable inorganic cation;

$R_1$ is ethyl or cyclopropyl;

$R_2$ and $R_3$ are the same or different and represent hydrogen, straight or branched $C_1$-$C_4$[,] alkylthio, $NHR_4$, $NR_4R_5$, trifluoromethyl, trifluoromethoxy, $NHCOR_6$, phenyl, phenoxy, phenylthio or phenylamino; wherein the phenyl moiety optionally is mono-substituted with fluoro;

$R_4$ and $R_5$ independently are hydrogen or straight or branched $C_1$-$C_4$ alkyl; or $R_4$ and $R_5$ together with the nitrogen to which they are bound, form a 5- or 6-membered ring

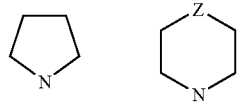

Z is $CH_2$, O, NH or $NCH_3$; and $R_6$ is $C_1$-$C_3$ alkyl, phenylamino, or phenyl optionally mono-substituted with $C_1$-$C_2$ alkoxy or fluoro;

with the proviso that $R_2$ and $R_3$ are not both hydrogen when X is $OCH_2$.

12. A method ['] of treating a disorder or condition selected from the group consisting of acute and chronic inflammation, rheumatoid arthritis, and transplant rejection in a mammal, comprising administering to the mammal in need of such treatment a therapeutically effective amount of a compound according to claim 1.[']

* * * * *